United States Patent [19]
Satterthwait, Jr. et al.

[11] Patent Number: 5,807,979
[45] Date of Patent: Sep. 15, 1998

[54] SYNTHETIC, THREE-DIMENSIONALLY STABILIZED POLYPEPTIDE MIMICS OF HIV

[75] Inventors: Arnold C. Satterthwait, Jr., Del Mar; Thomas Arrhenius; Lin-Chang Chiang, both of San Diego, all of Calif.; Edelmira Cabezas, Bogota, Colombia

[73] Assignee: The Scripps Research Institute, La Jolla, Calif.

[21] Appl. No.: 456,424

[22] Filed: Jun. 1, 1995

Related U.S. Application Data

[63] Continuation of Ser. No. 224,059, Apr. 7, 1994, abandoned, which is a continuation of Ser. No. 866,040, Apr. 8, 1992, abandoned, which is a continuation-in-part of Ser. No. 746,064, Aug. 12, 1991, abandoned, which is a continuation of Ser. No. 607,645, Oct. 29, 1990, abandoned, which is a continuation of Ser. No. 179,160, Apr. 8, 1988, abandoned.

[51] Int. Cl.$^6$ .......................... C07K 7/54; C07K 14/155
[52] U.S. Cl. ........................ 530/317; 530/317; 530/323; 530/387.1
[58] Field of Search ................... 530/317, 323, 530/387.1

[56] References Cited

U.S. PATENT DOCUMENTS 4,803,261  2/1989  Coy et al. ................................ 530/333

FOREIGN PATENT DOCUMENTS 0127234  12/1984  European Pat. Off. .
0185320   6/1986  European Pat. Off. .
0257742   3/1988  European Pat. Off. .

OTHER PUBLICATIONS

Satterthwait et al., Vaccine, vol. 6, pp. 99–103 (Apr. 1988).
Arrhenius et al., Peptides, Proceedings of the 11$^{th}$ American Peptide Symposium, Jul. 9–14, 1989, La Jolla, Calif., U.S.A. River et al. (Ed.) pp. 870–872.
Chiang et al., Proceedings of the 21$^{st}$ European Peptide Symposium, Giralt et al., (Ed.), Escom Science, Leiden, the Netherlands, pp. 465–467 (1991) (Peptides 1990).
Rudinger, *Peptide Hormones* (1976) University Park Press, Baltimore, Maryland, pp. 1–7.
Arrhenius et al., *Protein Structure, Folding, and Design 2* (1987) Alan R. Liss, Inc., pp. 453–465.
Arrehenius et al., "Covalent hydrogen bond mimics: An approach to shaping peptides" *DuPont/UCLA Presentation* (Apr. 11, 1987) 7 pages total.
Hruby, "Conformational restrictions of biologically active peptides via amino acid side chain groups" *Life Sciences* (1982) 31(3):189–199.
Arrhenius et al., "The chemical synthesis of structured peptides using covalent hydrogen–bond mimics" *Chem Abstracts* (1987) vol. 109, Abstract No. 73892w.
Satterthwait et al., "Conformational restriction of peptidyl immunogens with covalent replacements for the hydrogen bond" *Chem. Abstracts* (1988) vol. 109, Abstract No. 4898r.
Martinez et al., "Synthesis and biological activities of some pseudo–peptide analogues of tetragastrin: The importance of the peptide backbone" *J. Med. Chem.* (1985) 28:1874–1879.
Arrhenius et al., Peptides, Proceedings of the 11th Annual Peptide Symposium, Jul. 9–14, 1989, La Jolla, CA, USA, Rivier et al., eds., pp. 870–872.
Chiang et al., Proceedings of the 21st European Peptide Symposium, Giralt et al., eds., Escom Science, Leiden, The Netherlands, (1991) pp. 465–476.

*Primary Examiner*—Ponnathapura Achutamurthy
*Assistant Examiner*—T. D. Wessendorf
*Attorney, Agent, or Firm*—Donald G. Lewis

[57] ABSTRACT

Methods for synthesizing three-dimensional stabilized peptides which mimic the three-dimensional configuration of the active site of a natural, biologically active protein are carried out by (1) noting the three-dimensional configuration of the active site of a known biologically active protein (2) noting the amino acid sequence and the hydrogen bonds existing between amino acids which hydrogen bonds are capable of maintaining the three-dimensional configuration of the active site and (3) producing a synthetic three-dimensional peptide to mimic the structure of the active site. The synthetic peptide is synthesized so as to have the same or a similar amino acid sequence to the amino acid sequence of the active site of the biologically active polypeptide but with the stabilizing hydrogen bonds being replaced by a bridging divalent radical selected from the group of —(N)—C(CH$_3$)=N(H$^+$)—CH$_2$—(N)—; —(N)—C(CH$_3$)=N(H$^+$)—CH$_2$—CH$_2$—(N)—; and —(N)—N=CH—CH$_2$—CH$_2$—CH$_2$—(C)—. The stabilized three-dimensional peptide obtained is then isolated from the reaction mixture. The invention makes it possible to produce a wide range of biologically active compounds which have stable three-dimensional structures which allow the compounds to be used to obtain, for example, stabilized three-dimensional peptides which mimic the antigenic sites on viral envelopes which are useful as vaccines.

5 Claims, 3 Drawing Sheets

HIV(1)

SEQUENCE LISTING ( 1 ) GENERAL INFORMATION:

( i i i ) NUMBER OF SEQUENCES: 145

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:1:

```
    Ile  Glu  Ser  Leu  Asp  Ser  Tyr
    1              5
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:2:

Met  His  Ile  Glu  Ser  Leu  Asp  Ser  Tyr  Thr  Cys
1                   5                        10

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Ile  Glu  Ser  Leu  Asp  Ser  Tyr
1                   5

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Met  His  Ile  Glu  Ser  Leu  Asp  Ser  Tyr  Thr  Cys
1                   5                        10

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Cys  Thr  Arg  Pro
1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Thr  Arg  Pro  Asn
1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Arg Pro Asn Asn
1

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Pro Asn Asn Asn
1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Asn Asn Asn Thr
1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Asn Asn Thr Arg
1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Asn Thr Arg Lys
1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Thr Arg Lys Ser
1

( 2 ) INFORMATION FOR SEQ ID NO:13:

( i ) SEQUENCE CHARACTERISTICS:
   ( A ) LENGTH: 4 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:13:

Arg Lys Ser Ile
1

( 2 ) INFORMATION FOR SEQ ID NO:14:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:14:

Lys Ser Ile His
   1

( 2 ) INFORMATION FOR SEQ ID NO:15:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:15:

Ser Ile His Ile
   1

( 2 ) INFORMATION FOR SEQ ID NO:16:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:16:

Ile His Ile Ile
   1

( 2 ) INFORMATION FOR SEQ ID NO:17:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:17:

His Ile Ile Gly
   1

( 2 ) INFORMATION FOR SEQ ID NO:18:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:18:

Ile Ile Gly Pro
1

( 2 ) INFORMATION FOR SEQ ID NO:19:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:19:

Ile Gly Pro Gly
1

( 2 ) INFORMATION FOR SEQ ID NO:20:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:20:

Gly Pro Gly Arg
1

( 2 ) INFORMATION FOR SEQ ID NO:21:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:21:

Pro Gly Arg Ala
1

( 2 ) INFORMATION FOR SEQ ID NO:22:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:22:

Arg Ala Phe Tyr
1

( 2 ) INFORMATION FOR SEQ ID NO:23:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:23:

Gly Arg Ala Phe
1

( 2 ) INFORMATION FOR SEQ ID NO:24:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Ala Phe Tyr Thr
1

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Phe Tyr Thr Thr
1

( 2 ) INFORMATION FOR SEQ ID NO:26:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

Tyr Thr Thr Gly
1

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

Thr Thr Gly Glu
1

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

Thr Gly Glu Ile
1

( 2 ) INFORMATION FOR SEQ ID NO:29:

( i ) SEQUENCE CHARACTERISTICS:
   ( A ) LENGTH: 4 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:29:

Gly Glu Ile Ile
1

( 2 ) INFORMATION FOR SEQ ID NO:30:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:30:

Glu Ile Ile Gly
1

( 2 ) INFORMATION FOR SEQ ID NO:31:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:31:

Ile Ile Gly Asp
1

( 2 ) INFORMATION FOR SEQ ID NO:32:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:32:

Ile Gly Asp Ile
1

( 2 ) INFORMATION FOR SEQ ID NO:33:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:33:

Gly Asp Ile Arg
1

( 2 ) INFORMATION FOR SEQ ID NO:34:

( i ) SEQUENCE CHARACTERISTICS:
      ( A ) LENGTH: 4 amino acids
      ( B ) TYPE: amino acid
      ( D ) TOPOLOGY: linear (  i  i  ) MOLECULE TYPE: peptide (  x  i  ) SEQUENCE DESCRIPTION: SEQ ID NO:34:

Asp Ile Arg Gln
1

( 2 ) INFORMATION FOR SEQ ID NO:35:

(  i  ) SEQUENCE CHARACTERISTICS:
( A ) LENGTH: 4 amino acids
( B ) TYPE: amino acid
( D ) TOPOLOGY: linear (  i  i  ) MOLECULE TYPE: peptide (  x  i  ) SEQUENCE DESCRIPTION: SEQ ID NO:35:

Ile Arg Gln Ala
1

( 2 ) INFORMATION FOR SEQ ID NO:36:

(  i  ) SEQUENCE CHARACTERISTICS:
( A ) LENGTH: 4 amino acids
( B ) TYPE: amino acid
( D ) TOPOLOGY: linear (  i  i  ) MOLECULE TYPE: peptide (  x  i  ) SEQUENCE DESCRIPTION: SEQ ID NO:36:

Arg Gln Ala His
1

( 2 ) INFORMATION FOR SEQ ID NO:37:

(  i  ) SEQUENCE CHARACTERISTICS:
( A ) LENGTH: 4 amino acids
( B ) TYPE: amino acid
( D ) TOPOLOGY: linear (  i  i  ) MOLECULE TYPE: peptide (  x  i  ) SEQUENCE DESCRIPTION: SEQ ID NO:37:

Gln Ala His Cys
1

( 2 ) INFORMATION FOR SEQ ID NO:38:

(  i  ) SEQUENCE CHARACTERISTICS:
( A ) LENGTH: 4 amino acids
( B ) TYPE: amino acid
( D ) TOPOLOGY: linear (  i  i  ) MOLECULE TYPE: peptide (  x  i  ) SEQUENCE DESCRIPTION: SEQ ID NO:38:

Ala His Cys Asn
1

( 2 ) INFORMATION FOR SEQ ID NO:39:

(  i  ) SEQUENCE CHARACTERISTICS:
( A ) LENGTH: 4 amino acids
( B ) TYPE: amino acid
( D ) TOPOLOGY: linear (  i  i  ) MOLECULE TYPE: peptide (  x  i  ) SEQUENCE DESCRIPTION: SEQ ID NO:39:

His Cys Asn Ile
1

( 2 ) INFORMATION FOR SEQ ID NO:40:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

Cys Asn Ile Ser
1

( 2 ) INFORMATION FOR SEQ ID NO:41:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Asn Ile Ser Arg
1

( 2 ) INFORMATION FOR SEQ ID NO:42:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Ile Ser Arg Ala
1

( 2 ) INFORMATION FOR SEQ ID NO:43:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Ser Arg Ala Lys
1

( 2 ) INFORMATION FOR SEQ ID NO:44:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

Arg Ala Trp Asn
1

( 2 ) INFORMATION FOR SEQ ID NO:45:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:45:

Ala Lys Trp Asn
1

( 2 ) INFORMATION FOR SEQ ID NO:46:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:46:

Lys Trp Asn Asn
1

( 2 ) INFORMATION FOR SEQ ID NO:47:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:47:

Trp Asn Asn Thr
1

( 2 ) INFORMATION FOR SEQ ID NO:48:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:48:

Asn Asn Thr Leu
1

( 2 ) INFORMATION FOR SEQ ID NO:49:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:49:

Glu Glu Val Val
1

( 2 ) INFORMATION FOR SEQ ID NO:50:

( i ) SEQUENCE CHARACTERISTICS:
    ( A ) LENGTH: 4 amino acids
    ( B ) TYPE: amino acid
    ( D ) TOPOLOGY: linear (i i) MOLECULE TYPE: peptide (x i) SEQUENCE DESCRIPTION: SEQ ID NO:50:

Glu Val Val Ile
1

(2) INFORMATION FOR SEQ ID NO:51:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:51:

Val Val Ile Arg
1

(2) INFORMATION FOR SEQ ID NO:52:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:52:

Val Ile Arg Ser
1

(2) INFORMATION FOR SEQ ID NO:53:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:53:

Ile Arg Ser Glu
1

(2) INFORMATION FOR SEQ ID NO:54:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:54:

Arg Ser Glu Asn
1

(2) INFORMATION FOR SEQ ID NO:55:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:55:

Ser Glu Asn Phe
1

( 2 ) INFORMATION FOR SEQ ID NO:56:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

Glu Asn Phe Thr
1

( 2 ) INFORMATION FOR SEQ ID NO:57:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:57:

Asn Phe Thr Asp
1

( 2 ) INFORMATION FOR SEQ ID NO:58:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:58:

Phe Thr Asp Asn
1

( 2 ) INFORMATION FOR SEQ ID NO:59:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:59:

Thr Asp Asn Ala
1

( 2 ) INFORMATION FOR SEQ ID NO:60:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:60:

Asp Asn Ala Lys
1

( 2 ) INFORMATION FOR SEQ ID NO:61:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:61:

Asn Ala Lys Thr
1

( 2 ) INFORMATION FOR SEQ ID NO:62:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:62:

Ala Lys Thr Ile
1

( 2 ) INFORMATION FOR SEQ ID NO:63:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:63:

Lys Thr Ile Ile
1

( 2 ) INFORMATION FOR SEQ ID NO:64:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:64:

Thr Ile Ile Val
1

( 2 ) INFORMATION FOR SEQ ID NO:65:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:65:

Ile Ile Val His
1

( 2 ) INFORMATION FOR SEQ ID NO:66:

( i ) SEQUENCE CHARACTERISTICS:
  ( A ) LENGTH: 4 amino acids
  ( B ) TYPE: amino acid
  ( D ) TOPOLOGY: linear (i i) MOLECULE TYPE: peptide (x i) SEQUENCE DESCRIPTION: SEQ ID NO:66:

Ile Val His Leu
1

(2) INFORMATION FOR SEQ ID NO:67:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:67:

Val His Leu Asn
1

(2) INFORMATION FOR SEQ ID NO:68:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:68:

His Leu Asn Glu
1

(2) INFORMATION FOR SEQ ID NO:69:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:69:

Leu Asn Glu Ser
1

(2) INFORMATION FOR SEQ ID NO:70:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:70:

Asn Glu Ser Val
1

(2) INFORMATION FOR SEQ ID NO:71:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:71:

Glu Ser Val Gln
1

( 2 ) INFORMATION FOR SEQ ID NO:72:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:72:

Ser Val Gln Ile
1

( 2 ) INFORMATION FOR SEQ ID NO:73:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:73:

Val Gln Ile Asn
1

( 2 ) INFORMATION FOR SEQ ID NO:74:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:74:

Gln Ile Asn Cys
1

( 2 ) INFORMATION FOR SEQ ID NO:75:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:75:

Ile Asn Cys Thr
1

( 2 ) INFORMATION FOR SEQ ID NO:76:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:76:

Asn Cys Thr Arg
1

( 2 ) INFORMATION FOR SEQ ID NO:77:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:77:

Cys Thr Arg Pro
    1

(2) INFORMATION FOR SEQ ID NO:78:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:78:

Thr Arg Pro Asn
    1

(2) INFORMATION FOR SEQ ID NO:79:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:79:

Arg Pro Asn Tyr
    1

(2) INFORMATION FOR SEQ ID NO:80:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:80:

Pro Asn Tyr Asn
    1

(2) INFORMATION FOR SEQ ID NO:81:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:81:

Asn Tyr Asn Lys
    1

(2) INFORMATION FOR SEQ ID NO:82:

(i) SEQUENCE CHARACTERISTICS:
        (A) LENGTH: 4 amino acids
        (B) TYPE: amino acid
        (D) TOPOLOGY: linear (i i) MOLECULE TYPE: peptide (x i) SEQUENCE DESCRIPTION: SEQ ID NO:82:

Tyr Asn Lys Arg
1

(2) INFORMATION FOR SEQ ID NO:83:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:83:

Asn Lys Arg Lys
1

(2) INFORMATION FOR SEQ ID NO:84:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:84:

Lys Arg Lys Arg
1

(2) INFORMATION FOR SEQ ID NO:85:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:85:

Arg Lys Arg Ile
1

(2) INFORMATION FOR SEQ ID NO:86:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:86:

Lys Arg Ile His
1

(2) INFORMATION FOR SEQ ID NO:87:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:87:

Arg Ile His Ile
1

(2) INFORMATION FOR SEQ ID NO:88:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:88:

Ile His Ile Gly
1

(2) INFORMATION FOR SEQ ID NO:89:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:89:

His Ile Gly Pro
1

(2) INFORMATION FOR SEQ ID NO:90:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:90:

Ile Gly Pro Gly
1

(2) INFORMATION FOR SEQ ID NO:91:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:91:

Gly Pro Gly Arg
1

(2) INFORMATION FOR SEQ ID NO:92:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:92:

Pro Gly Arg Ala
1

(2) INFORMATION FOR SEQ ID NO:93:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:93:

Gly Arg Ala Phe
1

( 2 ) INFORMATION FOR SEQ ID NO:94:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:94:

Arg Ala Phe Tyr
  1

( 2 ) INFORMATION FOR SEQ ID NO:95:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:95:

Ala Phe Tyr Thr
  1

( 2 ) INFORMATION FOR SEQ ID NO:96:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:96:

Phe Tyr Thr Thr
  1

( 2 ) INFORMATION FOR SEQ ID NO:97:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:97:

Tyr Thr Thr Lys
  1

( 2 ) INFORMATION FOR SEQ ID NO:98:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:98:

Thr Thr Lys Asn
1

( 2 ) INFORMATION FOR SEQ ID NO:99:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:99:

Thr Lys Asn Ile
1

( 2 ) INFORMATION FOR SEQ ID NO:100:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:100:

Lys Asn Ile Gly
1

( 2 ) INFORMATION FOR SEQ ID NO:101:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:101:

Asn Ile Gly Thr
1

( 2 ) INFORMATION FOR SEQ ID NO:102:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:102:

Ile Gly Thr Ile
1

( 2 ) INFORMATION FOR SEQ ID NO:103:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:103:

Gly Thr Ile Arg
1

( 2 ) INFORMATION FOR SEQ ID NO:104:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:104:

Thr Ile Arg Gln
1

( 2 ) INFORMATION FOR SEQ ID NO:105:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:105:

Ile Arg Gln Ala
1

( 2 ) INFORMATION FOR SEQ ID NO:106:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:106:

Arg Gln Ala His
1

( 2 ) INFORMATION FOR SEQ ID NO:107:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:107:

Gln Ala His Cys
1

( 2 ) INFORMATION FOR SEQ ID NO:108:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:108:

Ala His Cys Asn
1

( 2 ) INFORMATION FOR SEQ ID NO:109:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:109:

His Cys Asn Ile
1

( 2 ) INFORMATION FOR SEQ ID NO:110:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:110:

Cys Asn Ile Ser
1

( 2 ) INFORMATION FOR SEQ ID NO:111:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:111:

Asn Ile Ser Arg
1

( 2 ) INFORMATION FOR SEQ ID NO:112:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:112:

Ile Ser Arg Ala
1

( 2 ) INFORMATION FOR SEQ ID NO:113:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:113:

Ser Arg Ala Lys
1

( 2 ) INFORMATION FOR SEQ ID NO:114:

( i ) SEQUENCE CHARACTERISTICS:
    ( A ) LENGTH: 4 amino acids
    ( B ) TYPE: amino acid
    ( D ) TOPOLOGY: linear (i i) MOLECULE TYPE: peptide (x i) SEQUENCE DESCRIPTION: SEQ ID NO:114:

Arg Ala Lys Trp
1

(2) INFORMATION FOR SEQ ID NO:115:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:115:

Ala Lys Trp Asn
1

(2) INFORMATION FOR SEQ ID NO:116:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:116:

Lys Trp Asn Asp
1

(2) INFORMATION FOR SEQ ID NO:117:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:117:

Trp Asn Asp Thr
1

(2) INFORMATION FOR SEQ ID NO:118:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:118:

Asn Asp Thr Leu
1

(2) INFORMATION FOR SEQ ID NO:119:

(i) SEQUENCE CHARACTERISTICS:
  (A) LENGTH: 4 amino acids
  (B) TYPE: amino acid
  (D) TOPOLOGY: linear (i i) MOLECULE TYPE: peptide (x i) SEQUENCE DESCRIPTION: SEQ ID NO:119:

Asp Thr Leu Arg
1

( 2 ) INFORMATION FOR SEQ ID NO:120:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:120:

Thr Leu Arg Gln
1

( 2 ) INFORMATION FOR SEQ ID NO:121:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:121:

Leu Arg Gln Ile
1

( 2 ) INFORMATION FOR SEQ ID NO:122:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:122:

Arg Gln Ile Val
1

( 2 ) INFORMATION FOR SEQ ID NO:123:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:123:

Gln Ile Val Ser
1

( 2 ) INFORMATION FOR SEQ ID NO:124:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:124:

Ile Val Ser Lys
1

( 2 ) INFORMATION FOR SEQ ID NO:125:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:125:

Val Ser Lys Leu
1

( 2 ) INFORMATION FOR SEQ ID NO:126:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:126:

Ser Lys Leu Lys
1

( 2 ) INFORMATION FOR SEQ ID NO:127:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:127:

Lys Leu Lys Glu
1

( 2 ) INFORMATION FOR SEQ ID NO:128:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:128:

Leu Lys Glu Gln
1

( 2 ) INFORMATION FOR SEQ ID NO:129:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:129:

Lys Glu Gln Phe
1

( 2 ) INFORMATION FOR SEQ ID NO:130:

( i ) SEQUENCE CHARACTERISTICS:
 ( A ) LENGTH: 4 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:130:

Glu Gln Phe Lys
1

( 2 ) INFORMATION FOR SEQ ID NO:131:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:131:

Gln Phe Lys Asn
1

( 2 ) INFORMATION FOR SEQ ID NO:132:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:132:

Phe Lys Asn Lys
1

( 2 ) INFORMATION FOR SEQ ID NO:133:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:133:

Lys Asn Lys Thr
1

( 2 ) INFORMATION FOR SEQ ID NO:134:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note="This position is Nuc Site."

( i x ) FEATURE:
        ( A ) NAME/KEY: Modified-site
        ( B ) LOCATION: 10
        ( D ) OTHER INFORMATION: /note="This position is (Acm)."

( i x ) FEATURE:
        ( A ) NAME/KEY: Modified-site
        ( B ) LOCATION: 17
        ( D ) OTHER INFORMATION: /note="This position is Cys-NH2."

( x i ) SEQUENCE DESCRIPTION: SEQ ID NO:134:

```
Leu Ala Xaa Ala Arg Gln Ala His Cys Xaa Asn Ile Ser Arg Ala Lys
1               5                   10                  15

Cys
```

( 2 ) INFORMATION FOR SEQ ID NO:135:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 7
        ( D ) OTHER INFORMATION: /note="This position is (Acm)."

( x i ) SEQUENCE DESCRIPTION: SEQ ID NO:135:

```
Ala Arg Gln Ala His Cys Xaa Asn Ile Ser Arg Ala Lys Cys
1               5                   10
```

( 2 ) INFORMATION FOR SEQ ID NO:136:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note="This position is NucSite."

( i x ) FEATURE:
        ( A ) NAME/KEY: Modified-site
        ( B ) LOCATION: 18
        ( D ) OTHER INFORMATION: /note="This position is Y-NH2."

( x i ) SEQUENCE DESCRIPTION: SEQ ID NO:136:

```
Leu Ala Xaa Ala Glu Ala Ala Lys Ala Ala Ala Ala Lys Arg Ala Gln
1               5                   10                  15

Gly Tyr
```

( 2 ) INFORMATION FOR SEQ ID NO:137:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:137:

```
Ile Glu Ser Leu Asp Ser Tyr
1               5
```

( 2 ) INFORMATION FOR SEQ ID NO:138:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:138:

```
Gly Leu Ala Gly
```

(2) INFORMATION FOR SEQ ID NO:139:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:139:

```
Arg  Gln  Ala  His  Cys  Asn  Ile  Ser  Arg  Ala  Lys
 1              5                        10
```

(2) INFORMATION FOR SEQ ID NO:140:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:140:

```
Cys  Thr  Arg  Pro  Asn  Asn  Asn  Thr  Arg  Lys  Ser  Ile  His  Ile  Gly  Pro
 1              5                        10                       15

Gly  Arg  Ala  Phe  Tyr  Thr  Thr  Gly  Glu  Ile  Ile  Gly  Asp  Ile  Arg  Gln
               20                        25                       30

Ala  His  Cys  Asn  Ile  Ser  Arg  Ala  Lys
               35                   40
```

(2) INFORMATION FOR SEQ ID NO:141:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (xi) SEQUENCE DESCRIPTION: SEQ ID NO:141:

```
Ala  Arg  Gly  Pro  Gly  Ile
 1              5
```

(2) INFORMATION FOR SEQ ID NO:142:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (xi) SEQUENCE DESCRIPTION: SEQ ID NO:142:

```
Gly  Phe  Ala  Arg  Gly  Pro  Gly  Ile  Ser
 1              5
```

(2) INFORMATION FOR SEQ ID NO:143:

(i) SEQUENCE CHARACTERISTICS:
        (A) LENGTH: 11 amino acids
        (B) TYPE: amino acid
        (D) TOPOLOGY: circular (ii) MOLECULE TYPE: peptide (xi) SEQUENCE DESCRIPTION: SEQ ID NO:143:

-continued

```
Gly  Tyr  Phe  Ala  Arg  Gly  Pro  Gly  Ile  Ser  Ile
 1              5                        10
```

(2) INFORMATION FOR SEQ ID NO:144:

(i) SEQUENCE CHARACTERISTICS:
        (A) LENGTH: 13 amino acids
        (B) TYPE: amino acid
        (D) TOPOLOGY: circular (ii) MOLECULE TYPE: peptide (xi) SEQUENCE DESCRIPTION: SEQ ID NO:144:

```
Gly  Thr  Tyr  Phe  Ala  Arg  Gly  Pro  Gly  Ile  Ser  Ile  Ser
 1              5                        10
```

(2) INFORMATION FOR SEQ ID NO:145:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /note="This site is [LeuAla] NucSite Ala."

(xi) SEQUENCE DESCRIPTION: SEQ ID NO:145:

```
Gly  Cys  Gly  Gly  Leu  Val  Met  Lys  Glu  Lys  Gln  Phe  Leu  Ala
 1              5                        10
```

SYNTHETIC, THREE-DIMENSIONALLY STABILIZED POLYPEPTIDE MIMICS OF HIV

CROSS-REFERENCES

This application is a continuation of application Ser. No. 08/224,059, filed Apr. 7, 1994, abandoned, which is a continuation of abandoned U.S. application Ser. No. 07/866,040, filed Apr. 8, 1992, which is a continuation-in-part of U.S. application Ser. No. 07/746,064 filed Aug. 12, 1991, now abandoned, which is a file-wrapper continuation of abandoned U.S. application Ser. No. 07/607,645, filed Oct. 29, 1990, which is a file-wrapper continuation of abandoned U.S. application Ser. No. 07/179,160, filed Apr. 8, 1988, which applications are incorporated herein by reference, and which applications we claim priority to under 35 USC § 120.

This invention was made with government support under government contracts DPE-5979-A-00-1035-00 from the United States Agency for International Development (USAID), and 2 P01 AI19499 from the National Institutes of Health (NIH). The government has certain rights in the invention.

TECHNICAL FIELD

The invention relates generally to peptide chemistry and synthesis. In particular, it relates to the synthesis of peptides which mimic the three-dimensional conformation of all or a part of another peptide, polypeptide or protein by the replacement of one or more naturally occurring hydrogen bonds with a covalent bond to stabilize the molecules.

BACKGROUND ART

It has been well understood for decades that the three-dimensional conformation of a protein, as much as its primary amino acid sequence, is determinative of the effectiveness of the protein in its biological function. To some degree, of course, the three-dimensional conformation is an automatic consequence of the primary structure in the appropriate environment. However, a large component in the factors accounting for the three-dimensional conformation is the ability of the components of the amide linkages to form interchain and mostly intrachain hydrogen bonds.

It is also known that sidechain amides participate in hydrogen bond linkages. The active regions of many proteins comprise relatively few amino acids. However, when the amino acid sequences of these active regions are isolated from the rest of the protein they generally show little or no activity. This is because short polypeptides (e.g., <20 aa) are unstable as regards their overall three dimensional structure and become disordered in $H_2O$ and/or under physiological conditions, i.e., they lose the three-dimensional structure which is provided when the short peptide is present in a longer protein.

Nature orders these active sequences by incorporating them into larger amino acid sequences, i.e., proteins where collective forces (e.g., intrachain hydrogen bonds) induce a three-dimensional structure. Accordingly, attempts have been made to stabilize the appropriate three-dimensional conformation of short peptides using linkages that are resistant to disruption. The three major approaches to such stabilization include cyclizing, forming disulfide bridges and using modified amino acids. These approaches are described briefly below.

First, peptides have been cyclized by linking N- and C-termini in an amide bond to provide similar shapes to those of the corresponding native proteins. C. M. Deber et al., *Acct Chem Res* (1976) 9:106; D. F. Veber et al., *Nature* (1981) 292:55. This approach is most effective with relatively small peptides, such as somatostatin. In the Deber paper, for example, a bicyclic analog was shown to have a potency equal or greater than that of somatostatin.

In a second approach, disulfide bridges are formed in vitro to stabilize conformation. See, for example, A. Ravi et al., *Tetrahedron* (1984) 40:2577; R. Kishore et al., *J Am Chem Soc* (1985) 107:2986. These papers concern stabilization of β-turn conformations in a series of cyclic peptides, and β-sheets in cyclic peptides, respectively.

Finally, turn structures have been rigidified by utilizing modified amino acid sidechains in cyclization reactions. See, for example, R. M. Freidinger et al., *Science* (1980) 210:656; J. L. Krstenansky et al., *Biochem Biophys Res Commun* (1982) 109:1368; D. S. Kemp et al., *Tetrahedron Lett* (1982) 23:3759; D. S. Kemp et al., *Tetrahedron Lett* (1982) 23:3761; U. Nagai et al., *Tetrahedron Lett* (1985) 26:647; M. Feigel et al., *J M Chem Soc* (1986) 108:181; M. Kahn et al., *Tetrahedron Lett* (1986) 27:4841. For example, the Nagai paper describes the synthesis of a bicyclic amino acid which had an almost superimposable conformation on that of D-Ala-L-Pro of a type II β-turn in (D-Ala)-gramicidin. The Freidinger paper describes the synthesis of an LHRH analog using a lactam conformation constraint in the component amino acids.

T. Arrhenius et al., in a preview of the below-described work, presented at the UCLA/DuPont Protein Structure Meeting in April 1987 a poster which suggested the use of covalent substitutes for hydrogen bonding in helices, β-sheets, and turns, and described a hydrazone linkage substitute for an i→i+4 hydrogen bond. This appears to be the first suggestion that hydrogen bonding can be covalently replaced by alternative covalent linkages. This and analogous substitutions would have the advantage of providing a reliable and easily used method for assuring conformation in a wide variety of peptides. The construct was further described in Arrhenius et al., (1987) Protein Structure and Design (UCLA Symposium on Molecular and Cellular Biology) 69:453–465. The following describes that work as per our earlier patent applications and provides further disclosure on new methods of synthesis and structures of biologically active, stabilized structures.

SUMMARY OF THE INVENTION

The present invention involves the synthesis of a stabilized, three-dimensional peptide which mimics the three-dimensional structure of an active site of biologically active, naturally occurring protein. The procedures of the invention are carried out by determining (1) the amino acids and their sequence and (2) the approximate three-dimensional structural configuration of an active site of a naturally occurring biologically active protein. After determining the sequence and structural configuration, (3) one or more of the stabilizing hydrogen bonds are identified. After identifying a stabilizing hydrogen bond, (4) a synthetic peptide is produced with the same or only slightly modified amino acid sequence as the active site of the naturally occurring biologically active protein, wherein at least one of the stabilizing hydrogen bonds is replaced by the inclusion of a bridging divalent radical. In general, the hydrogen bond represented by H...O is replaced by a covalent bond formed from a spatially equivalent covalent linkage selected from the group consisting of —(N)—C(CH$_3$)=N(H$^+$)—CH$_2$—(N)—; —(N)—C(CH$_3$)=N(H$^+$)—CH$_2$—CH$_2$—(N)—; and —(N)—N=CH—CH$_2$—CH$_2$—CH$_2$—(C)—, where the atoms in parentheses denote atoms corresponding to the amide and carbonyl peptide backbone atoms, i.e., the latter link replaces —(N)—H...O=C(R)—NH—CH$_2$—(C). Two classes of such bonds are found, as described below. Because the synthetic peptide can be made to mimic the three-dimensional structure of only a portion of a biologically active protein, i.e., the active site, it is possible to produce relatively small peptides which produce the same biological activity as their larger naturally occurring counterparts.

In addition to providing a method for creating synthetic peptides which mimic the three-dimensional structure of an active site of a naturally occurring biologically active protein, the present invention encompasses the synthetic peptides themselves. These peptides have the amino acid sequences similar to those of the corresponding naturally occurring polypeptides, but include at least one stabilizing covalent bond positioned strategically within the molecule in order to create a stable three-dimensional configuration which mimics the active site of the naturally occurring biologically active protein.

The stabilizing covalent bonds within these peptides may occur at locations other than those of the natural hydrogen bonds in order to further stabilized the synthetic molecule produced. The covalent "hydrogen bond mimic" of the invention is placed in a position so as to produce a stabilized form which mimics the essentials of the three-dimensional configuration of the naturally occurring, biologically active polypeptide. The synthetic peptides of the present invention generally include only a single replacement of a naturally occurring hydrogen bond in that this is generally sufficient to stabilize the three-dimensional, conformational structure of the molecule. The stabilization with respect to even a single stabilizing H-bond mimic may be sufficient to encourage additional three-dimensional stabilizing linkages in the molecule. However, it may be necessary to substitute more than one hydrogen bond with a spatially equivalent covalent linkage especially where the structure being mimicked includes more than one basic type of configuration, e.g., helical and loop configurations.

Those skilled in the art reading this disclosure will be able to determine the number of substitutions which will be necessary in order to stabilize the resulting synthetic molecule or such will be determined by experimentation carried out by following this disclosure. For example, it could be readily determined that only a single substitution is necessary in order to stabilize a helical structure. Once a single turn of the helix is established and its structural conformation locked into place, additional amino acid extensions on the helical chain will tend to form additional helical turns which are stabilized. Accordingly, the polypeptides which can be produced by Reaction Schemes 2, 3 and 5 can be directly useful in stabilizing helical structures and reverse turn configurations in the polypeptides derived therefrom.

A primary object of the present invention is to provide a method of synthesizing synthetic peptide molecules which have a three-dimensional structural configuration which mimics the three-dimensional structural configuration of the active site of a naturally occurring biologically active polypeptide.

Yet another object is to provide such a method wherein a hydrogen bond in a natural or synthetic amino acid sequence is replaced with a covalent mimic bond which is generally a double bond and is specifically a double bond between a carbon atom and a nitrogen group.

Another object is to provide such a method which uses solid phase synthesis methodology.

Still another object is to provide such a method which can be adapted to manual or automated solid phase synthesis technology.

Another object of the present invention is to provide biologically active peptides which have a stabilized three-dimensional configuration which mimic the three-dimensional configuration of an active site of a naturally occurring biologically active polypeptide.

An advantage of the present invention is that long amino acid chains as well as relatively small amino acid chains can be stabilized in terms of their three-dimensional structure so as to maintain and/or enhance their biological activity.

Another advantage is that the methodology of the invention need only be used to produce a mimic structure as regards a sterically accessible bioactive region of a larger protein.

Yet another advantage is that proteins produced using the methodology of the invention are highly stable under diverse conditions including changes in temperature and solvent.

Still another advantage is that cyclic peptides have increased biological stability with respect to degradation by natural processes.

A feature of the present invention is that the methodology disclosed herein can be used in order to create a wide range of different synthetic biologically active polypeptides.

Another feature is that the method of the invention can replace hydrogen bonds with covalent bond mimics to obtain any desired three-dimensional structure.

Yet another feature is that the method can be used with any amino acid sequence and as such can be used with a natural sequence or an artificial sequence, i.e., a sequence which does not correspond to a natural protein or a portion thereof.

Another feature is that the method can be used with sequences which include modified amino acids.

Another feature of the invention is that the method is adaptable to solid phase synthesis methodologies.

These and other objects, advantages and features of the present invention will become apparent to those persons skilled in the art upon reading the details of the structure, synthesis and usage of the methods and stabilized peptides as more fully set forth below, reference being made to the structural formulae and included specific examples forming a part hereof.

Detailed Description of Preferred Embodiments

Figure 1:
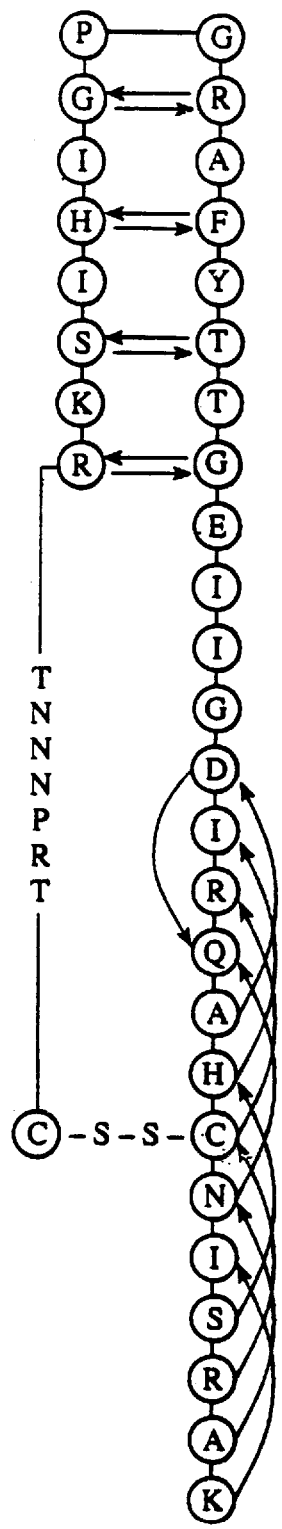
FIG. 1 is a schematic view showing the predicted regions of the secondary structure in a V3 loop wherein the arrows show the direction of hydrogen bond; NH→O=CNH and wherein ⒹⒹ→Ⓠ is for a side chain to the main chain H-bond.

Before the present method of synthesizing biologically active peptides which mimic the three-dimensional structure of the active site of natural protein and the synthetic peptides themselves are disclosed and described, it is to be understood that this invention is not limited to the particular methods and peptides described as such methods and peptides may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a hydrogen bond" includes a plurality of such hydrogen bonds, reference to "the bridging divalent radical" includes a plurality of such bridging radicals and reference to "an amino acid" includes a plurality of amino acids of the same type, and so forth.

A. Definitions

As used herein, "protein" and "polypeptide" and "peptide" are used interchangeably to designate polymers or oligomers formed by amide linkages of amino acids. Although the terms are used interchangeably, regardless of the number of amino acid residues in the resulting structure an effort has been made to refer to the generally small molecules of the invention as peptides and the large naturally occurring molecules with active sites as proteins. These terms are also used to denote structures which are fundamentally polymeric amino acids, even though one or more of said "amino acids" may be slightly modified to accommodate the linking moieties of the invention, or may be an amino acid analog. Unless otherwise noted, the amino acid residues are in the L configuration, but included within the invention are proteins which contain residues of the D configuration, as well as protein mixtures of enantiomeric forms of one or more amino acids. Additionally, one may include amino acids modified by substitution on the α-carbon and/or amide nitrogen or extensions to replacements for the amide nitrogen. Suitable substitutions include, for example, oxy, halo, alkyl of 1–6 carbons, acyl of 1–6 carbons, benzyl, haloalkyl of 1–6 carbons, and the like.

The term "peptide analog" as used herein refers to compounds of the invention, wherein one or more natural amino acids are replaced by amino acyl moieties bearing one of the covalent linkers of the invention. A peptide analog has the same nominal amino acid sequence as the segment of the protein (i.e., the active site) it mimics, and differs from the active site by including a covalent bond in place of one or more of the stabilizing hydrogen bonds in the natural active site sequence or remote from the site that acts to stabilize it.

"Hydrogen bond" is used in the conventional sense to designate the relatively weak, noncovalent interaction between a hydrogen atom and another more negative atom. More specifically, the hydrogen is covalently bonded to a carbon or to an electronegative atom, such as nitrogen, oxygen, or chlorine, which hydrogen atom is also "hydrogen bonded" to an unshared electron pair of an electron donor atom, such as O, N, or Cl. The geometry of the hydrogen bond approaches linearity between the electron donating atom, the hydrogen, and the atom to which it is attached; however, it is understood that a reasonable deviation from linearity is included, and indeed, usually found.

By "corresponding native peptide" is meant the effective portion of the protein which the peptide of the invention is intended to replace. Thus, for example, the invention includes analogs of the active site of LHRH, somatostatin, growth hormones, enzymes such as the various serine proteases, antiviral proteins such as the interferons, lymphokines such as TNF, lymphotoxin, and the colony-stimulating factors, immunodominant epitopes found on the surface of infective pathogens, and so forth. The three-dimensional conformation of the active sites are generally assured by virtue of hydrogen bonding at various locations by formation of intrachain and interchain linkages. Replacement of these hydrogen bonds by the spatially equivalent covalent linkage prepared by the method of the invention results in a peptide having substantially the same activity as and thus "corresponding to" the active site of a native protein.

By "spatially equivalent covalent linkage" is meant a substitute for the hydrogen bonding participants which linkage contains only covalent bonds, and which linkage holds the chains in essentially the same conformation as they would have been held by the hydrogen bonds. "Spatially equivalent" is also understood to accommodate minor deviations in exact spatial replication, so long as the resultant peptide has a biological activity. The activity may be greater than, less than, or preferably the same as the activity of the natural protein. The analog peptides of the invention may have antagonist activity, i.e., mimic the 3-D structure and thereby block the receptor site on the natural substrate and thereby hinder or eliminate the effect of natural proteins. For the purposes of the instant invention, "spatially equivalent covalent linkages" include —(N)—C($CH_3$)=N($H^+$)—$CH_2$—(N)—; —(N)—C($CH_3$)=N($H^+$)—$CH_2$—$CH_2$—(N)—; and —(N)—N=CH—$CH_2$—$CH_2$—$CH_2$—(C)—, where the atoms in parentheses denote atoms corresponding to the amide and carbonyl peptide backbone atoms, i.e., the latter link replaces —(N)—H...O=C(R)—NH—$CH_2$—(C). Even though the initial link is not strictly equivalent in length to the natural linkage it has been found to be useful in producing mimics.

B. General Description of the Invention

As indicated above, the invention includes methods of synthesizing peptides which mimic the three-dimensional structure of the active site of a naturally occurring protein and further includes the synthetic peptides, polypeptides and proteins produced by the methodology of this invention. The invention is carried out by first identifying a natural protein and a sterically accessible biologically active site of such a protein which provides for biological activity. After the protein fragment is identified, the amino acid sequence of a natural protein of interest is identified. Based on the sequence a structural prediction is made. To the extent possible, the three-dimensional structure is verified (e.g., forming a crystal and making and analyzing an x-ray diffraction pattern) and hydrogen bonds which stabilize that three-dimensional structure are determined. Methods of predicting and verifying the three-dimensional structure of a protein or portion thereof are described further below. Next, a peptide is synthesized using conventional synthesis technology (preferably automated solid phase technology) to obtain a peptide having an amino acid sequence that will lead to the three-dimensional conformation of the active site being mimicked. In general, the primary structure of the amino acid sequence will be identical or substantially identical to that of the corresponding protein. Then the novel chemistry of the present invention is used to include a covalent bond in place of a hydrogen bond to thereby lock the three-dimensional structure of the peptide in place. This is done by reacting a bridging, divalent radical with the amino acids in the peptide which are held in place by stabilizing hydrogen bonds. Accordingly, the invention can be used to mimic the three-dimensional structure of a wide range of different biologically active naturally occurring proteins. In addition to mimicking (to the extent possible) the three-dimensional structure of natural proteins, it is possible to vary the three-dimensional structure slightly in order to obtain an enhanced, a reduced, or a blocking effect as compared with the effect obtained by the natural protein.

C. Determining the Three-Dimensional Structure of a Protein or Active Site Thereof The present invention is not directly involved in recovering and/or analyzing proteins. More specifically, the present invention does not disclose a novel method of isolating, sequencing and/or further characterizing protein such as determining the biological activity, active sites and/or three-dimensional structures of a given protein. Procedures for doing such are known to those skilled in the art and new procedures will no doubt be developed in the future which procedures can then be used with the present invention.

Having made the above statement, it is clear that the practice of the present invention requires that one begin with some information on the protein of interest. The information can be as general as the DNA sequence which encodes the protein of interest to knowledge of an amino acid sequence and three-dimensional structure of the active site of a protein. In general, the more information available publicly on a given protein, the easier it is to adapt the methodology of the present invention to work with that protein. However, when little information is available, known procedures can be used to extract sufficient amounts of information so that the procedure of the present invention can be used.

When only the DNA sequence is known, the genetic code can be used to determine the amino acid sequence. Once the amino acid sequence is known, there are a number of computer programs available which can generate a probable three-dimensional structure. (See J. F. Gibrat et al. (1987), J. Mol. Biol. 198:425–443). The reliability of such programs is continually improving and their reliability is very high when used to determine the three-dimensional structure of certain sequences which tend toward certain three-dimensional configurations. Such programs can be applied to an entire sequence or to a sterically accessible region thought to be the active site.

Common Configurations in Proteins

It is highly probable that any given protein will include a sterically accessible bioactive region which includes one of the following known configurations.

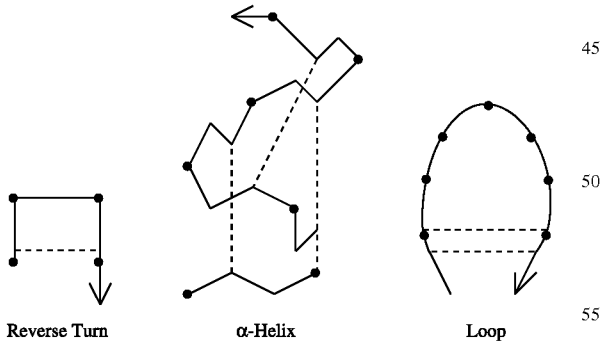

Reverse Turn    α-Helix    Loop

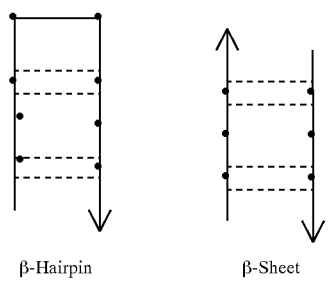

β-Hairpin    β-Sheet

Hydrogen-bonding patterns of common secondary structures α-carbon (•), carboxyl terminus (->); $C_\alpha$—CO—NH—$C_\alpha$—CO (•--•->); amide-amide hydrogen bond (---).

Any of the above configurations can be stabilized by the use of the bridging divalent radical of the invention whereby stabilizing hydrogen bonds are replaced with the covalently bound linking groups of the invention. For example, the β-hairpin loop can be stabilized to form the following specific stabilized structures:

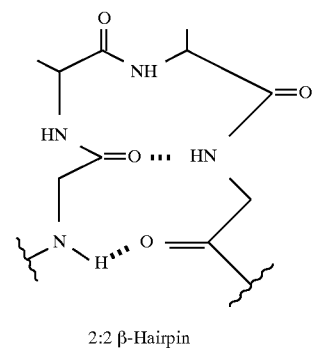

2:2 β-Hairpin Loop

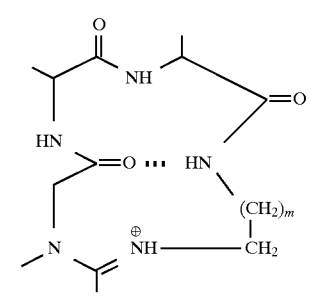

Loop with Class 1 Mimic

In another example, the alpha helix can also be stabilized. The circled letters indicate alpha carbons and side chains for amino acids according to the one letter amino acid code.

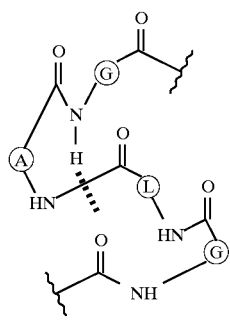

SEQ ID NO: 138   α-helix

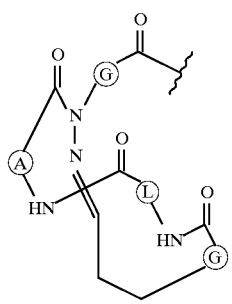

α-helix with
Class 2 mimic

In addition to computer programs, one can use X-ray crystallography techniques as well as NMR spectroscopy to determine the three-dimensional structure of purified proteins and portions thereof. Further, the three-dimensional structure and activity of some proteins is known and all that is required is the retrieval of such information followed by the application of the methodology of the present invention. After the stabilized structures of the invention are made, the same techniques and procedures used to determine the three-dimensional structure of the protein can be used to confirm that the stabilized peptides mimic the structure they were intended to mimic.

It is of course possible to apply a variety of techniques to obtain as much information as possible about the three-dimensional structure of a protein of interest. Regardless of the techniques used, amino acid sequence information must be obtained and information on the structural conformation of a sterically accessible region which is putatively the active site must be sufficient such that a determination can be made as to the location of a hydrogen bond which stabilizes the three-dimensional configuration of that active site. When such information is obtained or is already available, the methodology of the present invention can be applied in order to produce a peptide which includes a covalent bond that mimics the hydrogen bond of the natural protein and thereby stabilizes the three-dimensional structure of the peptide in substantially the same conformation as the active site of the protein.

D. Synthesis of Peptide Analogs

The peptides are produced by first attaching the amino acids to each other using procedures known to those skilled in the art, i.e., conventional peptide synthesis including automated solid phase synthesis. The result of such conventional procedures will be a peptide with the desired amino acid sequence but with no particular stable three-dimensional structure. In particular, the three-dimensional conformation will change continually when the peptide is in water or a physiological environment due to the weakness of the stabilizing hydrogen bonds. The essence of the present invention is the modification of such a structurally unstable peptide so as to stabilize the three-dimensional structure in water and/or an in vivo environment.

The stabilization is carried out by including a stabilizing covalent bond. This can be done, for example, by replacing a hydrogen bond existing between two amino acids in the natural protein with a covalent bond between corresponding (or closely positioned (e.g., 2–2000 amino acids)) amino acids or modified forms thereof in the synthetic peptide. The covalent bond permanently stabilizes the configuration of the two attached amino acids and thereby provides sufficient structural orientation so that the other amino acids in the peptide will align in their natural three-dimensional conformation (using hydrogen bonds) which matches the natural three-dimensional conformation of the active site of the natural protein. Thus, adequate stabilization of the mimic may be obtained by substitution of only one hydrogen bond by a covalent linkage. Furthermore, this stabilization may occur in a generic portion of the molecule to which a desired amino acid sequence may be coupled, the generic stabilized portion generating the correct three-dimensional structure in the target peptide.

The amino acids in natural proteins are connected by hydrogen bonds which appear as follows:

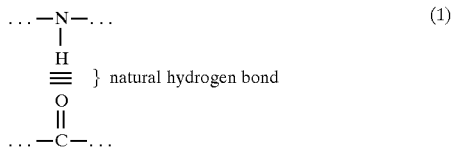   (1)

The hydrogen bond must be replaced by a covalent double bond in order to stabilize the three-dimensional conformation of the molecule. The hydrogen bond can be replaced by a variety of molecular configurations which, when in place, tend to mimic the hydrogen bond as it exists in the whole natural protein.

With reference to the above natural double bond, it is pointed out that the hydrogen and oxygen atoms forming the double bond cannot be merely replaced by two different atoms without modifying the manner in which those atoms are attached to their respective nitrogen and carbon atoms, i.e., the hydrogen bond configuration is not changed to

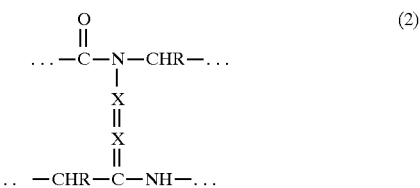   (2)

where each X is independently any atom of appropriate electron configuration. However, the natural hydrogen bond configuration can be changed to

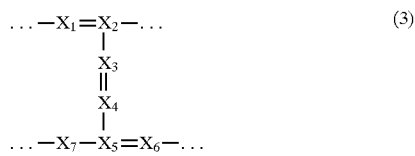   (3)

wherein $X_1$–$X_7$ are each independently an atom or molecular group of atoms with the required electron configuration allowing for the formation of the bonds shown.

The natural configuration can also be changed to

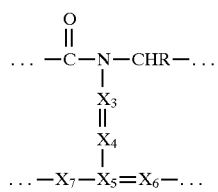 (4)

Yet another configuration is:

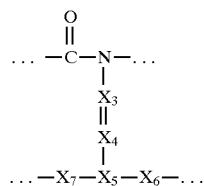 (5)

wherein $X_3$–$X_7$ are defined as above and $X_3$ and $X_4$ are preferably defined so to provide

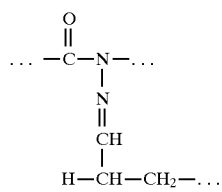 (5a)

or alternatively

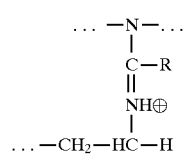 (5b)

R is hydrogen or an alkyl containing 1–6 carbon atoms.

Further, $X_5$ and $X_6$ are preferably defined in structure (5) to provide

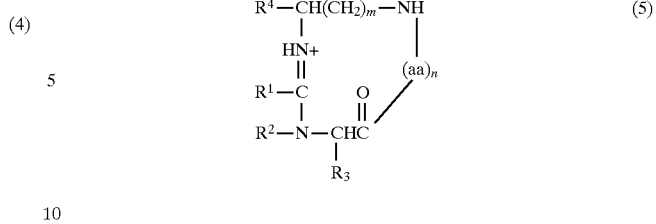 (5)

wherein $R^1$, $R^2$, and $R^3$ are each, independently, hydrogen or an alkyl moiety containing 1–6 carbon atoms, $R^4$ is any atom or molecular group of atoms with the required electron configuration, n is an integer from 1 to 2,000, and m is an integer of from 0 to 6.

E. Application to EGF Hormone

The methodology of the invention which includes hydrogen bond mimics may be used to make peptides which will find wide applications as pharmaceutical drugs, hormone replacements, diagnostic reagents, synthetic vaccines, completing reagents and catalysts. An illustrative example of such is an active fragment of epidermal growth factor (EGF), comprising amino acids 20–31 (A. Komoriya et al., *Proc Nat Acad Sci USA* (1984) 81:1351–55).

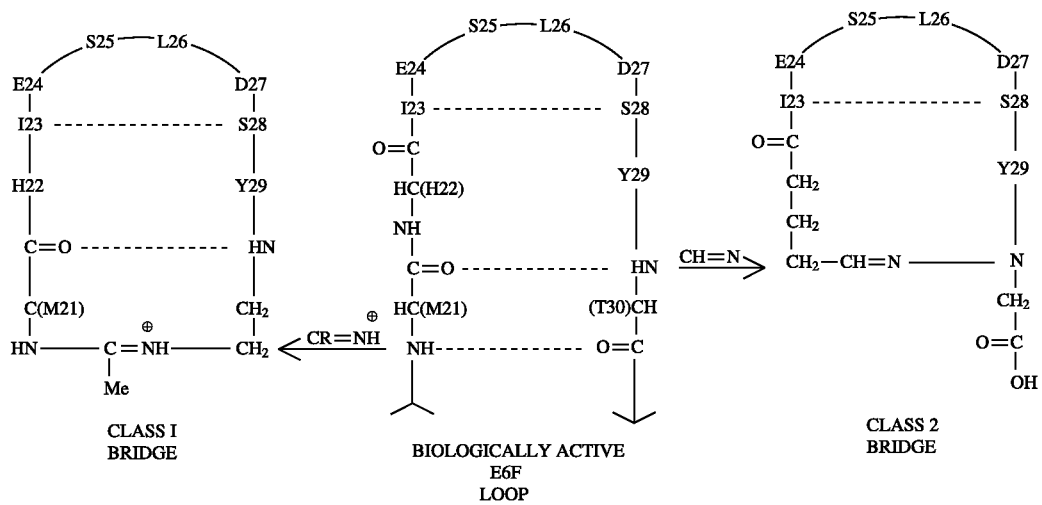

The peptide's activity is about $10^{-4}$ that of the parent molecule. The decreased activity was attributed to a loss, i.e., change in structure. In the intact protein, residues 20–23 and 28–31 form anti-parallel β-sheets, joined by residues 24–27 in a reverse turn (G. T. Montellione et al., *Proc Nat Acad Sci USA*, 83:8594–98 (1986)). Either class of mimics of the present invention may be used to stabilize the conformation of the peptide fragment. For Example, a class 1 aminoethaneamidinium bridge (Scheme 3) might be used to stabilize the reverse turn structure between residues 24 and 27 and the M21(N—H):T30(C=O) hydrogen bond while a class 2 bridge might be used to stabilize the M21(C=O): T30(NH) hydrogen bond as shown above. Similarly, class 1 and class 2 bridges might be used to stabilize the hydrogen bonds which form between V19 and N32. Thus, by utilizing both bridges one may systematically replace each of the putative hydrogen bonds in the EGF peptide to give a series of EGF peptides derivatives of increasing size.

Covalent mimics may also be employed to conformationally restrict synthetic peptide vaccines. Peptides shaped to correspond to the three-dimensional surface of proteins should induce antibodies with binding pockets which closely complement the native protein surfaces. Three-dimensional complementarity between the antibody and protein surfaces should lead to tighter binding interactions and improve the affinity. The overall immune response to conformationally restricted peptides should show greater efficiency than the unrestricted peptides of the prior art.

In another example illustrating a potential use for this methodology, an EGF-like protein isolated from human malaria has been proposed as a candidate vaccine (D. C. Kaslow et al. (1988) Nature 333:74–76). Peptide sequences homologous to the EGF-like sequences from the malaria protein could be conformationally restricted in the same manner using Class I and Class II mimics for use as a synthetic vaccine.

F. Survey of Conformations and Hydrogen Bond Types

The results of a reasonable number of X-ray crystallographic studies of protein conformations have permitted the assessment of shapes and the assignment of the nature of hydrogen bonds securing these conformations at a molecular level. Certain conventions have been followed in designating the types of hydrogen bonds denoted. In general, the participants are designated in terms of a reference residue, i, and an additional residue (i+#) which is that residue which is located the designated number (#) of residues further downstream (starting from the N-terminus of the chain). The hydrogen bond itself is designated by an arrow which points in the direction of hydrogen donation—i.e., the arrow points from the residue donating the hydrogen toward the residue bearing the electrons that accept them. Thus, for example, an (i+4--->i) hydrogen bond is the donation of hydrogen from the nitrogen in the i+4 residue to the oxygen of the carbonyl group on the i residue 4 amino acids downstream. A hydrogen bond between these participants results in an α-helix.

Table 1 shows representative examples of the types of hydrogen bonds which are recognized to form commonly encountered conformational characteristics of single-chain and interchain-linked proteins. Some of these conformations are more frequently encountered than others. Approximately 80–90% of all globular proteins are found in the form of either α-helices, β-sheets, or β-turns, each of which is shown above as are other types of turns and helices which are less common. In Table 1, the type of hydrogen bond is shown along with the ring size—i.e., the number of atoms forming the resulting ring (including the electron-donating atom and the hydrogen). A detailed description of these structures is provided by J. S. Richardson, Advances in Protein Chemistry, 34:167 (1981); Dickerson R E, Geis I. (1980) in "The Structure and Action of Proteins." Benjamin/Cummings Publishing Co; Sibanda L S et al, J. Mol. Biol. 206:759–777 (1989); Wilmot C M and Thornton J M, J. Mol. Biol. 203:221–232 (1988). The resulting structures are shown as the type of secondary or tertiary structure obtained as a consequence of the hydrogen bond type given.

TABLE 1

| Hydrogen Bond | Ring Size | Secondary or Tertiary Structure |
|---|---|---|
| i + 2 → i | 7 | $2_7$ ribbon |
| i + 3 → i + 1 | 10 | $3_{10}$ helix; reverse turns of the Type I, I', II, II', III, IV, IVa, IVb etc. |
| i + 4 → i | 13 | alpha helix; 3:3 loop (rare, various) |
| i + 4 + n → i | 13 + 3n | n = 1–20; hairpin loops |
| i → i + 3 | 14 | 2:2 loop (defined types); 2:4 loop (unusual, various) |
| i → i + 3 + n | 14 + 3n | n = 1–20; hairpin loops |
| i + 5 → i | 16 | pi helix (hypothetical structure, never observed); 4:4 loop (defined and various) |
| i → i + 4 | 17 | 3:5 loop (defined and various) |
| i → i + 5 | 20 | 4:6 loop (many conformations) |

In addition to these intrachain linkages, antiparallel and parallel β-sheet hydrogen bonding can also be substituted by the covalent linkers of the invention. The schematics of these interchain bonds are as follows:

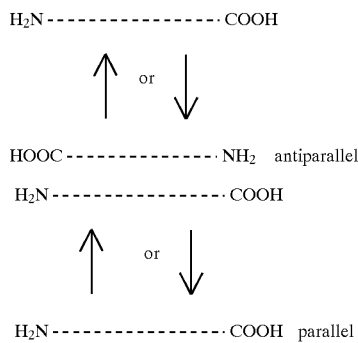

In addition to the foregoing, since the side chains of glutamine, aspartic acid, serine, glutamic acid, cysteine, threonine, lysine, arginine, histidine, tryptophan or tyrosine donate or accept hydrogen atoms, sidechain-sidechain and sidechain-backbone hydrogen bonds can be formed, for example, between two asparagine residues, asparagine and glutamine, or glutamine and glutamine, or between these amide sidechains and the backbone residues.

The covalent moieties which mimic the hydrogen bonds can be used to replace any of the foregoing linkages to maintain the desired secondary or tertiary structure.

G. Types of Hydrogen Bond Mimics

Two major classes of mimics have been found which are successful in replicating the geometry of the hydrogen bonds of native proteins. These are shown in comparison to the "Normal" or typical hydrogen bonds below as class 1 and class 2.

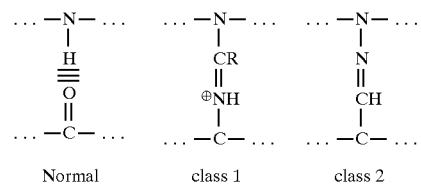

Class 1 utilizes an alkylamidine linkage in place of the hydrogen bond. The hydrogen of the hydrogen bond ordinarily attached to the α-amino group of the i amino acid is replaced by —CR=, wherein R is H or alkyl (1–6C) or an extended acid —$(CH_2)_n$—$CO_2H$ where n=1–6 and the electron pair donating oxygen of the carboxyl group of the i+# amino acid is replaced by —NH⊕=.

Class 2 of covalent linkers are hydrazone-hydrocarbon links. In this embodiment, the hydrogen of the α-amino of the i+# amino acid is replaced by a —N=, which is, in turn, covalently linked by a double bond to a —CH= residue which takes the place of the carboxyl oxygen of the i residue.

Either of the foregoing classes of mimics can be used in the hydrogen bond configurations shown in Table 1 and in the interchain bonds. In the preferred embodiments the Class I mimic substitutes in the i→i+n sense, while the Class II mimic substitutes in the i+n→i sense (Table 1). However, new syntheses can be written for substituting Class I and II mimics in the alternative fashion. Accordingly, the present invention makes it possible to substitute the —CR=NH (+)— and —N=CH— hydrogen bond mimics, or any double bond substitution for the hydrogen bond in either sense either backbone to backbone or side chain to backbone or side chain to side chain.

The synthesis of these mimics in the context of peptide chains is illustrated below. As also noted, modifications in the peptide chain in the immediate vicinity of the hydrogen bond mimics may also be included. When synthesized, the mimics may be chain-extended to form the remainder of the peptides using standard protein synthesis techniques.

One aspect of the invention is a stabilized polypeptide, which comprises a sequence of at least two amino acids or amino acid equivalents linked by peptide bonds, wherein at least one hydrogen bond of the formula (C)=O...H—(N) is replaced by a bridging covalent bond of the form —(N)—CR=NH⊕—(C)— or —(N)—N=CH—(C)—. Stabilized peptides of the invention may include 7–6,000 amino acids, 3–2,000 amino acids, 3–30 amino acids, or 10–20 amino acids. The method of the invention is most effective in low molecular weight peptides as stabilization by ordinary conformational folding and hydrogen bonding is enhanced in large proteins.

Preferred embodiments of the invention include those wherein the covalent hydrogen bond mimics of the invention form interchain links between atoms forming the backbone of the polypeptide. Additional preferred embodiments include those wherein side chain elements form intrachain linkages. A preferred subclass comprises the polypeptide where the amino acid chain and the hydrogen bond mimics are selected to form rings having 7, 10, 13, 13+3n, 14, 14+3n, 16, 17 or 20 atoms where n=1–20 as indicated in Table 1. However, these are only examples and rings of other sizes from 7–6,000 are not excluded.

One preferred class of compounds of the invention comprises the compounds of the formula

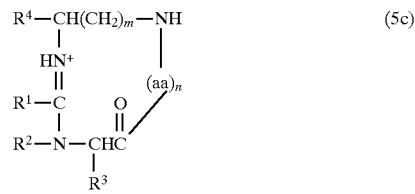

(5c)

wherein $(aa)_n$ is an amino acid sequence of 1–2000 (i.e., aa is an amino acid and n is an integer from 1 to 2,000). $R^4$ is a hydrogen, or alkyl moiety containing 1–6 carbon atoms, or an acid —$(CH_2)_p$—$(CO_2H)_p$=1–6 which can be extended with an amino acid sequence of 1–2000 amino acids, or an amino acid sequence of 1–2000 or a —NH—CHR—COOH or a =CH—CHR—COOH where R is the side chain of a natural or unnatural amino acid. m is an integer from 0–6. $R^1$ is hydrogen or alkyl (1–6) or an acid —$(CH_2)_n$—$CO_2H$, n=1–6 which can be extended by an amino acid sequence of 1–2000 amino acids. $R^2$ is H or alkyl (1–6C) or an amino acid sequence of 1–2000 amino acids and $R^3$ is the side chain of a natural or unnatural amino acid. A presently preferred compound is that wherein $(aa)_n$ is Ala—Ala, $R^4$ is hydrogen, m is 0, both $R^1$ and $R^2$ are methyl and $R^3$ is the side chain of glycine, i.e., H. Another presently preferred compound is the compound wherein $(aa)_n$ is Ala—Ala, $R^4$ is hydrogen, m is 1, both $R^1$ and $R^2$ are methyl and $R^3$ is H. Another presently preferred compound is the compound wherein $(aa)_n$ is Glu-Ser-Leu, $R^4$ is hydrogen, m is 1, both $R^1$ and $R^2$ are methyl and $R^3$ is H.

Another presently preferred class of compounds of the invention comprises the compounds of the formula:

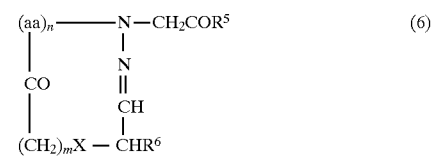

(6)

wherein $R^5$ is alkoxy of 1–6 carbons, phenoxy, naphthyloxy, benzoxy, —$NH_2$ or an amino acid sequence of 1–2,000 amino acids, $(aa)_n$ is an amino acid sequence of 1–2,000 amino acids, X is a nonentity, —$CH_2$—, —NH—, =CH— or =NH, with the double bonds to $CHR^6$, m is an integer from 0–5, and $R^6$ is a nonentity, H, —$NH_2$ with or without an amino acid extension of 1–2000 amino acids, alkyl (1–6C) or an alkyl amine $(CH_2)_n$—$NH_2$ where n=1–6 with or without an amino acid extension of 1–2000 amino acids. A presently preferred compound of the invention is that wherein $R^5$ is Et, $(aa)_n$ is Leu-Ala, X is —$CH_2$—, m is 1, and $R^6$ is H. Another presently preferred compound is the compound wherein $R^5$ is $NH_2$, $(aa)_n$ is SEQ ID NO:1, X is —$CH_2$—, m is 1 and $R^6$ is H. Another presently preferred compound is the compound wherein $R^5$ is $NH_2$, $(aa)_n$ is SEQ ID NO:2, X is —$CH_2$—, m is 1 and $R^6$ is H.

Synthesis of Class 1 Mimics

The basic reaction for formation of class 1 linkers can be conducted using a thioamide selectively activated with methyl iodide to yield a thioimidate which subsequently reacts with an unprotected primary amine according to the reaction:

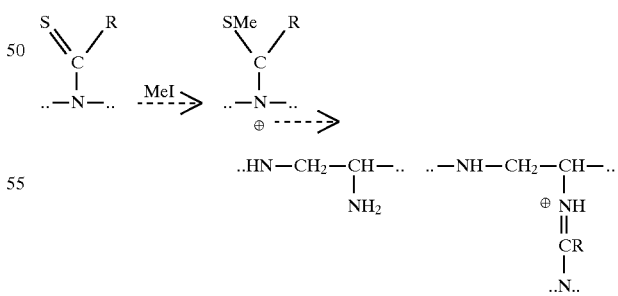

In the foregoing reaction and throughout this disclosure, "..-" indicates extension of the peptide chain.

Reaction scheme 1 shows the application of this reaction to the formation of the desired linkage in the context of the intrachain mimic:

Scheme 1(a)

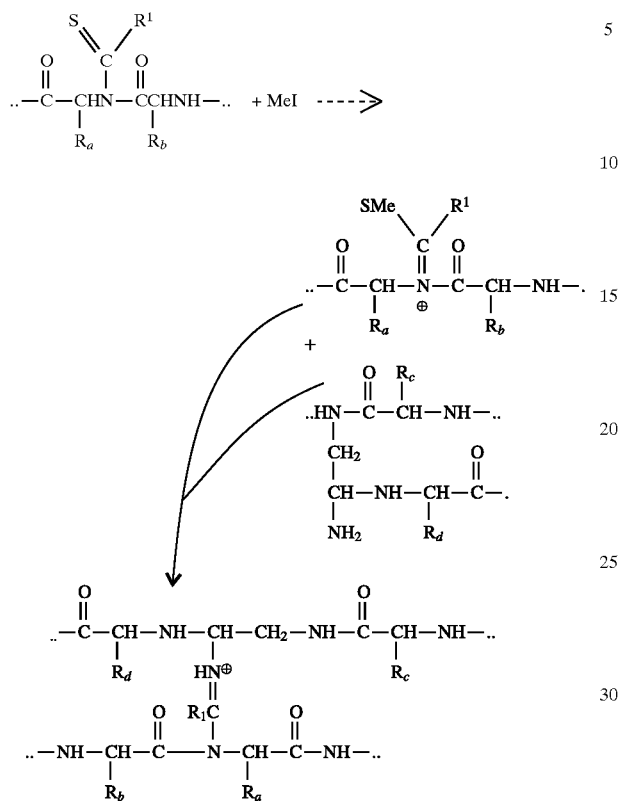

Reaction Scheme 1(b)

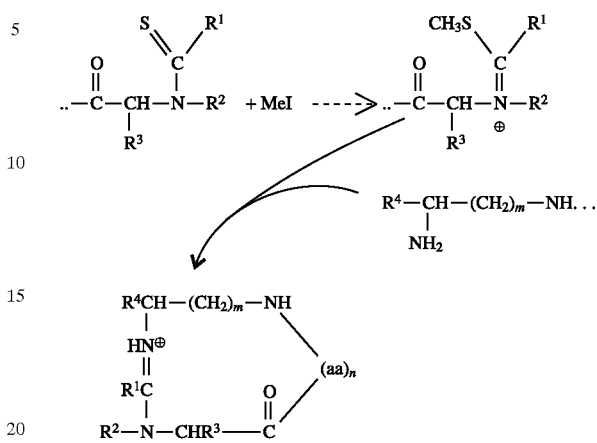

Reaction scheme 1(b) is formally identical to Scheme 1(a) and encompasses a preferred class of compounds of the invention (5).

For adaptation to peptide synthesis, the $R^4$— bearing residue is linked to an amino acid or a sequence of amino acids and a thiolamide analogue to yield an intermediate that is finally cyclized. For example, an i--->i+3 hydrogen bond is replaced in a 2:2 loop by placing a dipeptide intermediate to the residue containing the aminoethyl substituent and the residue containing the thioamide, according to reaction scheme 1(c).

Reaction Scheme 1(c)
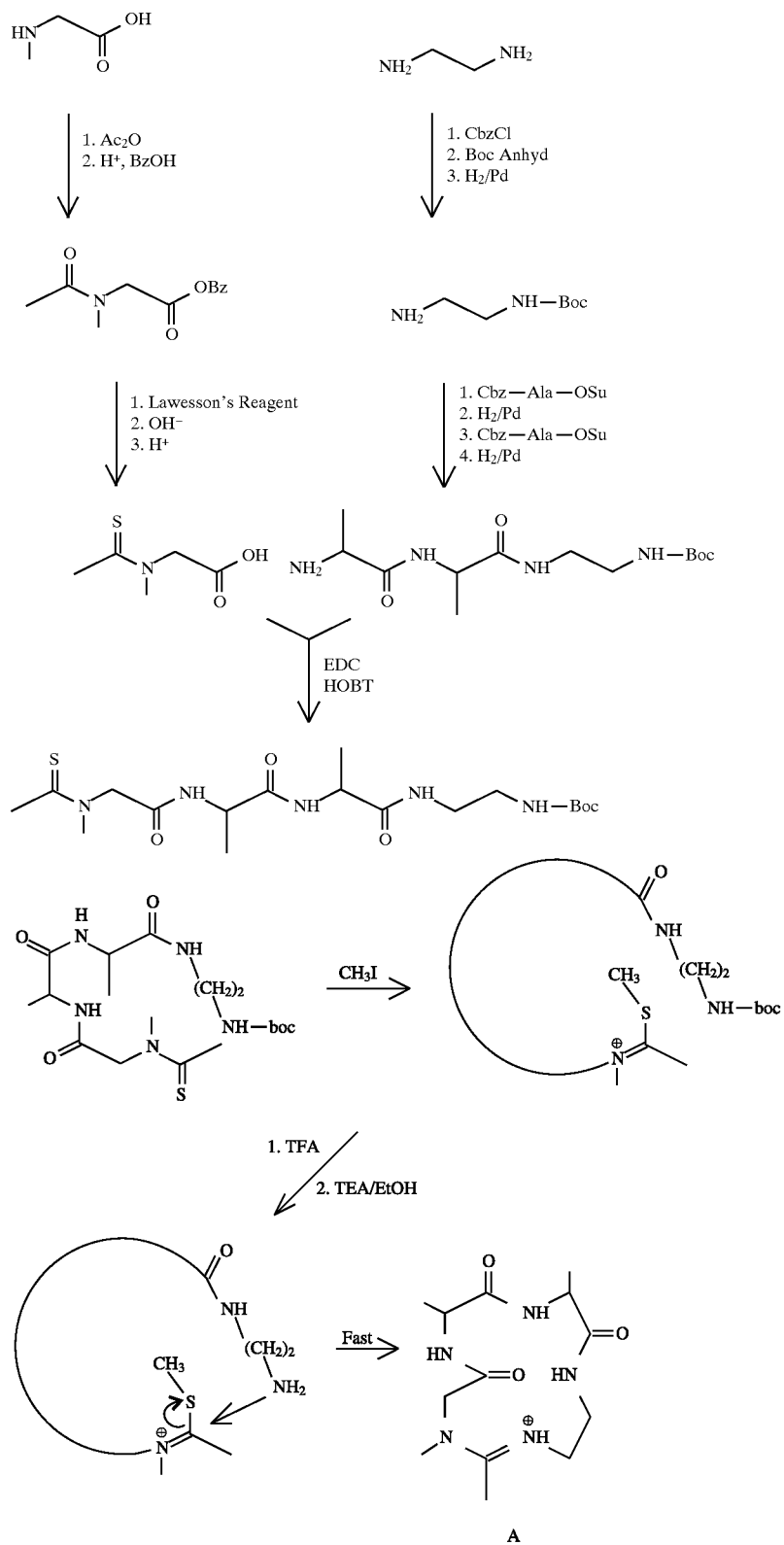
The basic reaction is the displacement of a methylthio substituent with a primary amine which is itself a alkylamino substituent to an amide nitrogen of the same or different chain in the peptide. According to the schematic used to illustrate the invention herein, the oxygen of the carbonyl which would have been the electron donor atom in the hydrogen bond is replaced by an =⊕NH—. On the other hand the former carbonyl carbon of the thiolamide which is converted to the central carbon of an amidinium group replaces the hydrogen which would have accepted the electron donation. As shown in reaction scheme 1(a) and 1(b), the resulting —CR=⊕NH— double bond replaces the donated electrons and the recipient hydrogen, i.e., the hydrogen bond.

The detailed chemistry for introducing a class 1 mimic into a peptide chain was developed in the context of a 2:2 loop and is depicted in Scheme 1(c). The reactions for each step are set forth in the Examples below. The structure of the final product was verified as folding the inserted peptide into a Type 1 reverse turn by both X-ray crystallography and in solutions of dimethyl sulfoxide or water using both one-dimensional and two-dimensional NMR spectroscopy. It has been established by X-ray crystallography that approximately 10% of the amino acids in globular proteins fold into the Type 1 reverse turn structure. C. W. Wilmot and J. M. Thornton, J. Mol. Biol. 203:221 (1988) Reverse turns provide a means for the polypeptide chain to fold back on itself allowing for a globular form. Consequently, they are located almost exclusively on protein surfaces where biological activity occurs. The reactions for each step are set forth in the Examples below.

In the Schemes below, the following abbreviations are used: Cbz=carbobenzoxy, Me=methyl, Et=ethyl, Bu=butyl, Ac=acetyl (CH₃C=O), DPPA=diphenylphosphoryl-azide, TEA=triethylamine, EDC=N-ethyl-N'-3-dimethylaminopropylcarbodiimide hydrochloride, HOBT=1-hydroxybenzotriazole, DMF=dimethyl formamide, TFA=trifluoroacetic acid, Ms=mesyl (methane sulfonyl), Bz=benzyl, Boc=t-butoxycarbonyl, THF=tetrahydrofuran, Im=imidazolyl, and DMAP=N,N-dimethylaminopyridine. All starting materials are either available from commercial sources, and/or are described in the literature.

Scheme 2

Step 1:

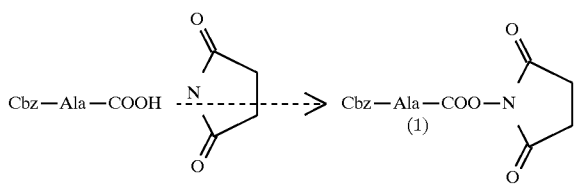

Step 2:

1 + Gly/EtOH/NaHCO₃ ----> Cbz—Ala—Gly (2)

Step 3:

2 + DPPA/TEA/t = BuOH ----> Cbz—Ala—C(O)NHCH₂NH—Boc (3)

Step 4:

3 + H₂/Pd, EtOH ----> NH₂—Ala—C(O)NHCH₂NH—Boc (4)

Step 5:

4 + 1, EtOH ----> Cbz—Ala—Ala—C(O)NHCH₂NH—Boc (5)

-continued
Scheme 2

Step 6:

5 + H₂/Pd, DMF ----> NH₂—Ala—Ala—C(O)NHCH₂NH—Boc (6)

Step 7:

MeNHCH₂COOH + HOCH₂(C₆H₅) ---->

MeNHCH₂COOCH₂(C₆H₅) (7)

Step 8:

7 + AcOAc + TEA ----> MeC(O)N(Me)CH₂COOCH₂(C₆H₅) (8)

Step 9:

8 + Lawesson's Rgnt ----> MeC(=S)N(Me)CH₂COOCH₂(C₆H₅) (9)

Step 10:

9 + NaOH/MeOH/H₂O ----> MeC(=S)N(Me)CH₂COOH (10)

Step 11:

6 + 10 + EDC/HOBT/DMF ---->

----> MeC(=S)N(Me)CH₂CO(Ala)₂NHCH₂NH—Boc (11)

Step 12:

11 + MeI/AcOH ---->

MeC=N⊕—(Me)CH₂CO(Ala)₂NHCH₂NH—Boc
|
SMe (12)

Step 13:

SMe
            |
12 + TFA ----> Me—C=N⊕—CH₂C(O)NH(Ala)₂—NHCH₂NH₂
            |
            (13)

Step 14:

13 + weak base ---->
ion exchange
resin/DMF

Me—C=N⊕—CH₂C(O)NH(Ala)₂—NHCH₂NH
    |
    Me                    (14)

Using similar chemistry, an aminoethane amidinium link (Class I link) was introduced in the context of replacing an i+i-->i+3 hydrogen bond in a 2:2 loop in Scheme 1c and Scheme 3 which follows. Each step of the reaction scheme is set forth in detail in the examples below.

Scheme 3

Step 1:

$$NH_2CH_2CH_2NH_2 + Cbz-Cl/MsOH/KOAc \longrightarrow Cbz-NHCH_2CH_2NH_2 \quad (15)$$

Step 2:

$$15 + (t-BuO)_2CO, EtOAc \longrightarrow Cbz-NHCH_2CH_2NH-Boc \quad (16)$$

Step 3:

$$16 + H_2/Pd, EtOH \longrightarrow NH_2CH_2CH_2NH-Boc \quad (17)$$

Step 4:

$$17 + 1, EtOH \longrightarrow Cbz-Ala-CONHCH_2CH_2NH-Boc \quad (18)$$

Step 5:

$$18 + H_2/Pd, EtOH \longrightarrow NH_2-Ala-CONHCH_2CH_2NH-Boc \quad (19)$$

Step 6:

$$19 + 1, EtOH \longrightarrow Cbz-(Ala)_2-CONHCH_2CH_2NH-Boc \quad (20)$$

Step 7:

$$20 + H_2/Pd, EtOH \longrightarrow NH_2-(Ala)_2-CONHCH_2CH_2NH-Boc \quad (21)$$

Step 8:

$$MeNHCH_2COOH + TsOH/BzOH/BzH \longrightarrow MeNHCH_2COOBz \quad (22)$$

Step 9:

$$22 + TEA/Ac_2O/THF \longrightarrow \underset{Me}{AcNCH_2COOBz} \quad (23)$$

Step 10:

$$23 + Lawesson's\ Rgt \longrightarrow \underset{Me}{\overset{S}{\underset{\|}{MeC}}-NCH_2COOBz} \quad (24)$$

Step 11:

$$24 + NaOH/MeOH/H_2O \longrightarrow \underset{Me}{\overset{S}{\underset{\|}{MeC}}-NCH_2COOH} \quad (25)$$

Step 12:

$$21 + 25 \longrightarrow \underset{Me}{\overset{S}{\underset{\|}{MeC}}-NCH_2CONH(Ala)_2-CONHCH_2CH_2NH-Boc} \quad (26)$$

Step 13:

$$26 + MeI/AcOH \longrightarrow \underset{Me}{\overset{SMe}{\underset{|}{MeC}}=\overset{\oplus}{N}-CH_2CONH(Ala)_2-CONHCH_2CH_2NH-Boc} \quad (27)$$

-continued
Scheme 3

Step 14:

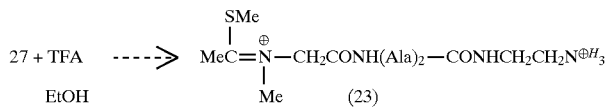

Step 15:

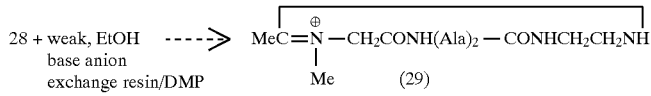

The structures of the final products from Scheme 2 and 3 were verified as folding the peptide into a Type 1 reverse turn in both dimethyl sulfoxide and water using one and two-dimensional nmr spectroscopy. 2D nmr experiments included COSY and ROESY experiments. The predicted temperature coefficients, Jan coupling constants and nuclear Overhauser enhancements for a Type 1 reverse turn (Wuthrich, K. In: NMR of Proteins and Nucleic Acids, J. Wiley & Sons, New York, p. 166 (1988)) are all observed for the final products of Scheme 2 and 3. An X-ray crystal structure for the product of Scheme 3 is also in agreement with the Type 1 reverse turn conformation. The reactions outlined in Scheme 3 have been used to synthesize six different compounds which incorporate different amino acids and display the same basic Type 1 reverse turn conformation (L. Chiang et al. (1990) In: Peptides 1990, Proceedings of the 21st European Peptide Symposium. Giralt E., Andreu D (eds). ESCOM Science, Leiden, the Netherlands, 1991, p 465)

It has been established by X-ray crystallography that approximately 10% of the amino acids in globular proteins fold into the Type 1 reverse turn structure and that the structure is located almost exclusively on the protein surface (P. Y. Chou and G. D. Fasman, J. Mol. Biol. (1977) 115:135; C. M. Wilmot and J. M. Thornton, J. Mol. Biol. (1988) 203:221) where biological reactions often occur (G. D. Rose et al., Adv. in Prot. Chem. (1985) 37:1).

Synthesis of Class 2 Mimics

The class 2 mimics are generated by reaction of a hydrazine derivative with an acetal or ketal according to the general reaction:

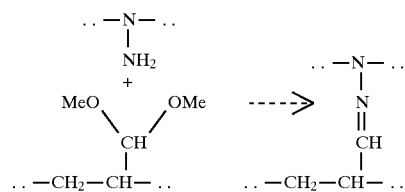

In the context of intrachain bonding, the reaction is as shown in Scheme 4.

In the case of a class 2 mimic, the hydrogen bond is replaced by the carbon-nitrogen double bond (C=N) of an N-acyl hydrazone. This hydrazone is formed by a condensation reaction between an N-amido peptide and a peptide fragment bearing an aldehyde moiety, masked in the form of an acetal. Scheme 4 outlines the synthesis of class 2-containing peptides. The synthesis is a convergent one. The two fragments 31 and 37 are synthesized in parallel, then combined in a peptide condensation reaction. In the final step, the hydrogen bond mimic is formed by a cyclocondensation reaction between the hydrazide and the acetal functional groups.

Three types of 31 fragment (31a, 31b, 31c) are illustrated.

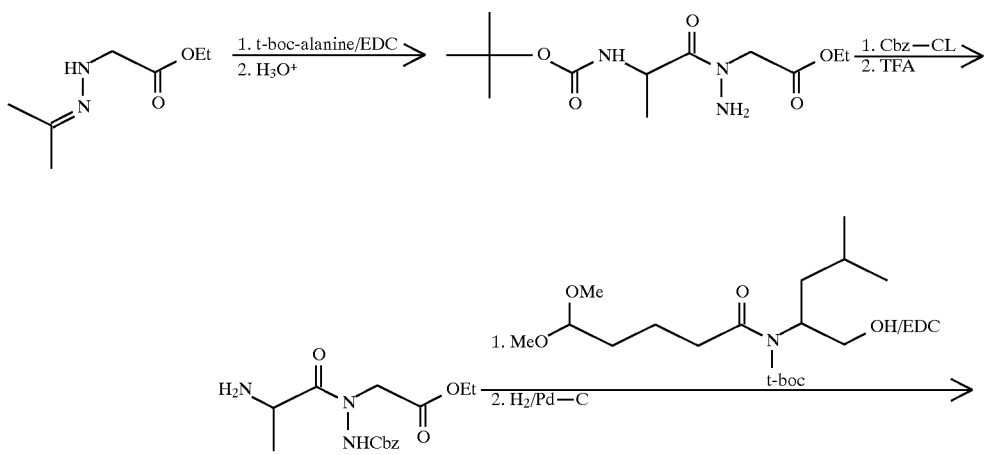

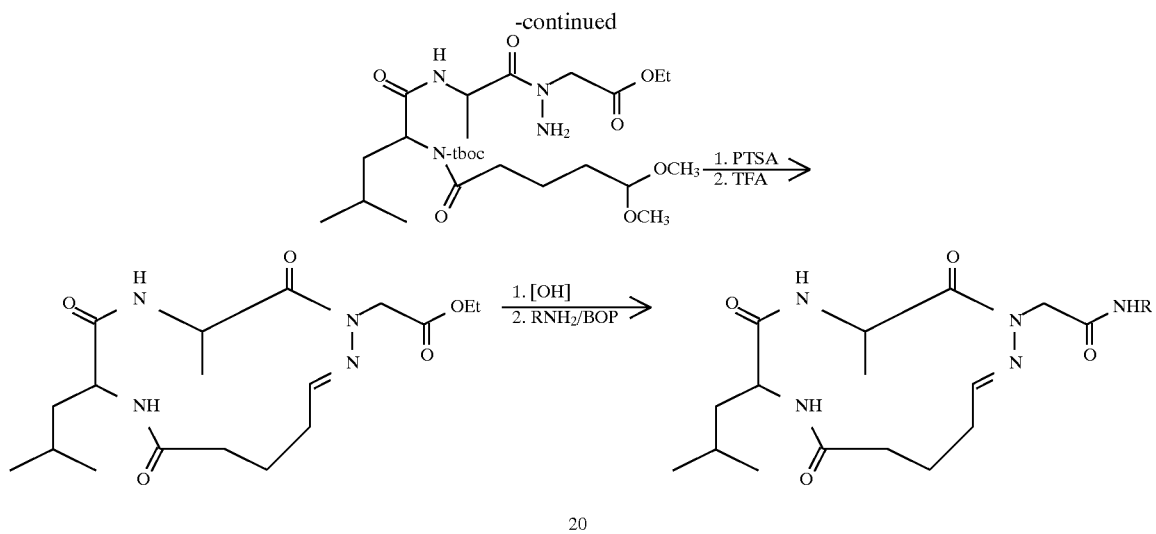

Reaction Scheme 4(a)

Reaction scheme 4(a) includes the reactions steps shown above in reaction scheme 1(a) applied to a preferred class of compounds.

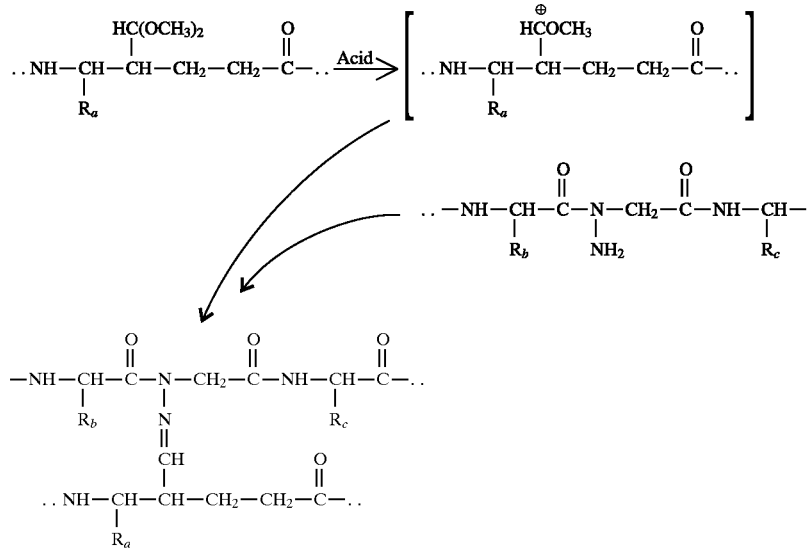

Reaction Scheme 4(b)

Yet another example of such a reaction is shown below.

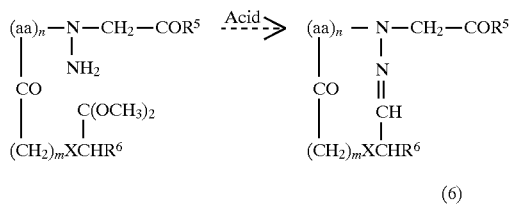

The synthesis of one particular peptide containing a class 2 hydrogen bond mimic is shown in Scheme 5. The experimental details are set forth in the examples below. All syntheses were characterized by NMR spectroscopy and high resolution mass spectroscopy. Detailed conformational analysis of these peptides were carried out using a combination of one and two-dimensional NMR techniques, including Difference Nuclear overhauser Effect spectroscopy, COSY spectroscopy, and coupling constant analysis. The product produced is helical in character.

Scheme 5

Step 1:

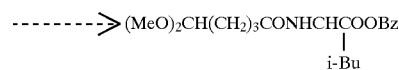

-continued
Scheme 5

Step 2:

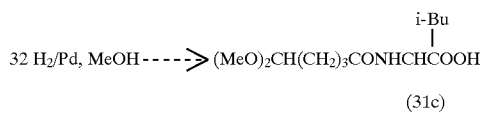
(31c)

Step 3:

H₂NNHCH₂COOEt + acetone ----> Me₂C=NNHCH₂COOEt
(34)

Step 4:

34 + (Boc—NHCHMeCO)₂O ---->

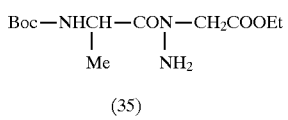
(35)

Step 5:

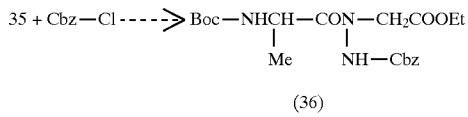
(36)

Step 6:

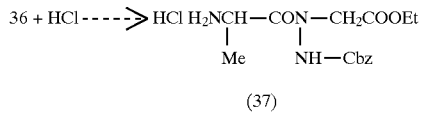
(37)

Step 7:

31c + 37 ---->

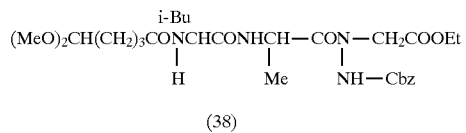
(38)

Step 8:

38 + H₂Pd ---->

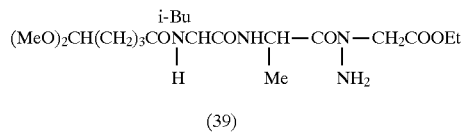
(39)

Step 9:

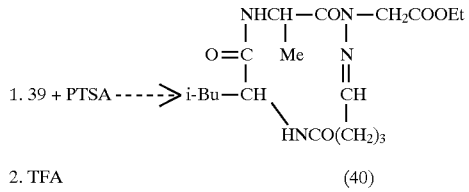

2. TFA                              (40)

Detailed conformational analysis of the final product alone and appended to short amino acid chains (6–11 amino acids) in trifluoroethanol and water was carried out using 1D and 2D nmr spectroscopy. Preliminary conformational studies have been reported (T. Arrhenius and A. C. Satterthwait In: Peptides: Chemistry, Structure and Biology. Proceedings of the Eleventh American Peptide Symposium. Riview J. E., Marshall, G. R. (eds) ESCOM Leiden, the Netherlands, p. 870 (1990); L.-C Chiang et al. In: Peptides 1990. Proceedings of the 21st European Peptide Symposium. Giralt E., Andreu D. (eds) ESCOM Science, Leiden, the Netherlands, 1991, p. 465). These studies utilize 1D and 2D NMR spectroscopy, including COSY, double quantum filter COSY, TOCSY experiments and selective deuterium labeling for the assignment of signals, measurements of Jan coupling constants, and the determination of deuterium exchange rates and temperature coefficients. Nuclear Overhauser enhancements (both short and midrange) were identified in 2D ROESY experiments. These studies are in complete agreement with prediction (K. Wuthrich et al., J. Mol. biol. 180:715 (1984)) and fully establish that the Class 2 mimic when substituted for an (i+4)–i hydrogen bond stabilizes peptides in the alpha helical conformation in trifluoroethanol and water at ambient and physiological temperatures.

Thus, both classes of mimic can be used to stabilize a conformation ordinarily stabilized by hydrogen bonding in the context of a growing peptide chain, or can be formed even more simply between parallel or antiparallel chains in sheets. This evidences the broad scope of utility of these mimics, which can be put into the context of any desired peptide.

EXAMPLES

The following examples are presented as a further illustration for the practitioner of ordinary skill in the art, and are not intended to limit the scope of the invention in any manner. The following examples demonstrate solution-phase synthesis; however, other methods (e.g., solid phase synthesis) are also considered within the scope of this invention.

Example 1

(Scheme 2, Step 1)

N-benzyloxycarbonyl-alanine N-hydroxy-succinimide ester (1) was synthesized according to the procedure described by G. W. Anderson et al., *J Am Chem Soc* (1964) 86:1839.

Briefly, equal moles of N-Cbz-ala, N-hydroxysuccinimide, and dicyclohexylcarbodiimide were added in THF in an ice-water bath with stirring. The mixture was kept in a cool room (0° C.) overnight. The dicyclohexylurea precipitate was removed by filtration, and the solvent evaporated in vacuo. The residue was crystallized from isopropanol to yield 1.

Example 2

(Scheme 2, Step 2)

Cbz-alanine N-hydroxysuccinimide ester (1, 20 mM) was dissolved in absolute ethanol (EtOH, 50 ml), and the solution added to a solution of glycine (20 mM) and NaHCO₃ (40 mM) in water (50 ml). The mixture was stirred at room temperature overnight, concentrated to a small volume with a rotary vacuum evaporator, and acidified to pH 2 with concentrated HC1. The product was crystallized by cooling the mixture in an ice-bath, and recrystallized from ethyl acetate-hexane to provide Cbz-Ala-Gly (2).

Example 3
(Scheme 2, Step 3)

Following the procedure of T. Shioiri et al., *J Am Chem Soc* (1972) 94:17, equal moles of Cbz-Ala-Gly (2), diphenylphosphorylazide (DPPA), and triethylamine (TEA) were dissolved in t-butanol. The mixture was refluxed overnight. After evaporation of the solvent, the neutral fraction in ethyl acetate obtained after aqueous acid and alkali work ups was purified by silica gel column chromatography or crystallization from ethyl acetate-hexane, to yield Cbz-Ala—CONHCH$_2$NH—Boc (3).

Example 4
(Scheme 2, Step 4)

To a solution of 3 (10 mM) in EtOH in a round bottom flask was added a small amount of Pd/C catalyst. A balloon filled with hydrogen was attached to the flask. After repeated degassing, the flask was filled with hydrogen and the mixture vigorously stirred for 30 min and filtered through celite to provide NH$_2$—Ala—CONHCH$_2$NH—Boc (4).

Example 5
(Scheme 2, Step 5)

Cbz-alanine N-succinimide ester (1, 10 mM) was added to the 4 product solution from Example 4. The mixture was agitated overnight and concentrated to a small volume with a rotary vacuum evaporator. The product was crystallized from the mixture with addition of distilled water to yield Cbz-Ala—Ala—CONHCH$_2$NH—Boc (5).

Example 6
(Scheme 2, Step 6)

Compound 5 was deprotected by catalytic hydrogenolysis using the procedure described in Example 4 above, to provide NH$_2$—Ala—Ala—CONHCH$_2$NH—Boc (6)

Example 7
(Scheme 2, Step 7)

Sarcosine (250 mM) and p-toluenesulfonic acid (TSOH, 255 mM) were added to a mixture of benzyl alcohol (100 ml) and toluene (50 ml). The mixture was heated to reflux, and the water formed by the reaction trapped in a Dean Stark receiver, a conical tube used for trapping water from a refluxing distillate. When no more water appeared in the distillate, the mixture was cooled to room temperature, added to ether, and cooled in an ice-water bath for two hr. The crystalline product was collected on a filter and recrystallized from CH$_2$Cl$_2$-Et$_2$O to yield MeNHCH$_2$COOCH$_2$(C$_6$H$_5$)TsOH (7).

Example 8
(Scheme 2, Step 8)

Acetic anhydride (AcOAc, 10 mM) was slowly added to a solution of 7 (10 mM) and TEA (20 mM) in THF with stirring. The mixture was left to stand at room temperature for 2 hr after the addition of acetic anhydride was completed. After the solvent was removed by vacuum evaporation the residue was redissolved in ethyl acetate and washed with citric acid (1M), NaHCO$_3$ (0.5M), MgSO$_4$. The produce was recovered by the removal of the solvent with a vacuum evaporator to yield AcN(Me)CH$_2$COOCH$_2$(C$_6$H$_5$) (8).

Example 9
(Scheme 2, Step 9)

Following the procedure described by S. Scheibye et al., *Bull Soc Chim Belg* (1978) 87:229, p-methoxyphenylthionophosphine sulfide (LAWESSON'S REAGENT™) was added to a solution of 8 in benzene, and the mixture heated to reflux for 10 min. After cooling, the mixture was washed with saturated NaHCO$_3$ solution, citric acid, water, saturated NaCl solution, and dried over anhydrous MgSO$_4$. After the solvent was removed by vacuum evaporation, the residue was crystallized from ethyl acetate-hexane to provide MeC(=S)N(Me)CH$_2$COOCH$_2$(C$_6$H$_5$) (9).

Example 10
(Scheme 2, Step 10)

A solution of N-thioacetyl sarcosine benzylester (9, 10 mM) in methanol (20 ml) was surrounded by a water bath of room temperature, and 1N NaOH (22 ml) was added with stirring. The mixture was left at room temperature for 2 hr and treated with strongly acidic ion exchangers. After the solvent was removed by vacuum evaporation, the residue was crystallized from EtOAc-hexane to yield MeC(=S)N(Me)CH$_2$COOH (10).

Example 11
(Scheme 2, Step 11)

An equimolar mixture of 6, 10, N-ethyl-N'-3-dimethylaminopropylcarbodiimide hydrochloride (EDC), and 1-hydroxybenzotriazole (HOBT) in dimethylformamide (DMF) were reacted at 0° C. overnight. The mixture was treated with mixed ion exchangers and the solvent removed by vacuum evaporation. The residue was crystallized from ethanol and water to yield the condensation product MeC(=S)N(Me)CH$_2$CO(Ala)$_2$NHCH$_2$NH—Boc (11).

Example 12
(Scheme 2, Step 12)

Compound 11 was dissolved in acetic acid and a molar excess of iodomethane added. After the mixture was stirred for 6 hr the solvent, the unreacted MeI was removed with a vacuum rotary evaporator. It was important to use acid acetic as solvent to stabilize the product in this step. Other solvents, such as DMF or THF resulted in a considerable side product formation. The reaction yielded

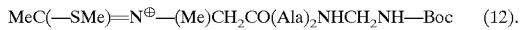

Example 13
(Scheme 2, Step 13)

Compound 12 was treated with trifluoroacetic acid (TFA) for 10 min, and the solvent removed by vacuum evaporation to provide

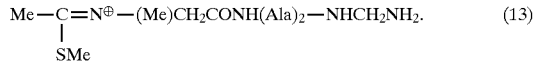

Example 14
(Scheme 2, Step 14)

Compound 13 was dissolved in DMF at a concentration less than 10 mM and treated with weakly basic anion exchange resins. After the solvent was removed by vacuum evaporation the residue was purified with HPLC to yield

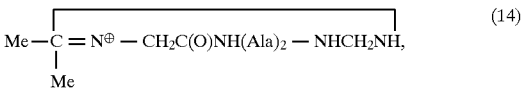

a compound of the invention.

Example 15
(Scheme 3, Step 1)

Following the procedure described by G. J. Atwell et al., *Synthesis* 1984:1032. Ethylene diamine (0.26M) was dissolved in water containing bromocresol green as indicator. Methanesulfonic acid (0.48M) in water 50 ml) was added until a blue to pale yellow color was achieved. The solution was diluted with EtOH (140 ml), vigorously stirred, and treated at room temperature with solutions of benzyloxycarbonyl chloride (Cbz—Cl, 0.23M) in dimethoxyethane (DME, 50 ml) and 50% aqueous KOAc. After the additions were complete the mixture was stirred for 1 hr, and volatiles were removed in vacuo. The residue was shaken with water (500 ml) and filtered to remove the bis-derivative. The filtrate was washed with benzene, basified with 40% NaOH, and then extracted with benzene. The organic layer was washed with saturated aqueous NaCl, dried with $MgSO_4$, and dried in vacuo to yield Cbz—$NHCH_2CH_2NH_2$ (15).

Example 16
(Scheme 3, Step 2)

Compound 15 was dissolved in ethyl acetate and an equimolar amount of t-butyl pyrocarbonate slowly added. The solution was dried with a vacuum rotary evaporator and the residue crystallized from ethyl acetate-hexane to yield Cbz—$NHCH_2CH_2NH$—Boc (16). (See P. L. Barker et al. J. Org. Chem 46:2455–2465 (1980).

Example 17
(Scheme 3, Step 3)

Following the procedure described in Example 4 above, compound 16 was hydrogenolyzed to provide $NH_2CH_2CH_2NH$—Boc (17). (See P. L. Barker et al. J. Org. Chem 46:2455–2465 (1980).

Example 18
(Scheme 3, Step 4)

Following the procedure described in Example 5 above, compounds 17 and 1 were condensed in EtOH to provide Cbz-Ala—$CONHCH_2CH_2NH$—Boc (18).

Example 19
(Scheme 3, Step 5)

Following the procedure described in Example 4 above, compound 18 was hydrogenolyzed to provide $NH_2$—Ala—$CONHCH_2CH_2NH$—Boc (19).

Example 20
(Scheme 3, Step 6)

Following the procedure described in Example 5 above, compounds 19 and 1 were condensed in EtOH to provide Cbz-Ala—Ala—$CONHCH_2CH_2NH$—Boc (20).

Example 21
(Scheme 3, Step 7)

Following the procedure described in Example 4 above, compound 20 was hydrogenolyzed to provide $NH_2$—Ala—Ala—$CONHCH_2CH_2NH$—Boc (21).

Example 22
(Scheme 3, Step 8)

Following the procedure described in Example 7 above, $MeNHCH_2COOH$ is esterified with benzyl alcohol to provide $MeNHCH_2COOBz$ (22).

Example 23
(Scheme 3, Step 9)

Following the procedure described in Example 8 above, compound 22 is acetylated to provide AcNH(Me)$CH_2COOBz$ (23).

Example 24
(Scheme 3, Step 10)

Following the procedure described in Example 9 above, compound 23 is converted to

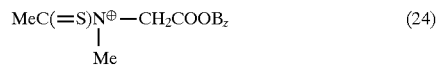

$$\text{MeC}(=S)N^{\oplus}\text{—CH}_2\text{COOBz} \quad (24)$$
$$|$$
$$\text{Me}$$

Example 25
(Scheme 3, Step 11)

Following the procedure described in Example 10 above, compound 24 is saponified to yield $$\text{MeC}(=S)N^{\oplus}\text{—(Me)CH}_2\text{COOH} \quad (25)$$

Example 26
(Scheme 3, Step 12)

Following the procedure described in Example 11 above, compounds 21 and 25 are condensed to provide $$\text{MeC}(=S)N^{\oplus}\text{—(Me)CH}_2\text{CONH(Ala)}_2\text{—}$$
$$\text{CONHCH}_2\text{CH}_2\text{NH—Boc} \quad (26)$$

Example 27
(Scheme 3, Step 13)

Following the procedure described in Example 12 above, compound 26 is S-methylated with MeI to provide $$\text{MeC}(\text{—SMe})=N^{\oplus}\text{—(Me)CH}_2\text{CONH(Ala)}_2\text{—}$$
$$\text{CONHCH}_2\text{CH}_2\text{NH—Boc} \quad (27)$$

Example 28
(Scheme 3, Step 14)

Following the procedure described in Example 13 above, compound 27 was deprotected by hydrolyzing the Boc group with TFA, thus providing $$\text{MeC}(\text{—SMe})=N^{\oplus}\text{—(Me)CH}_2\text{CONH(Ala)}_2\text{—}$$
$$\text{CONHCH}_2\text{CH}_2N^{\oplus}H_3 \quad (28).$$

Example 29
(Scheme 3, Step 15)

Following the procedure described in Example 14 above, compound 28 is cyclized with a weakly basic anion exchange resin to provide

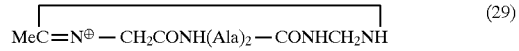

$$\overline{\text{MeC}=N^{\oplus}\text{ — CH}_2\text{CONH(Ala)}_2\text{ — CONHCH}_2\text{NH}} \quad (29)$$

a compound of the invention. Compound 29 exhibits a reverse turn structure, as determined by nmr. Also crystal structure determined.

Example 30
(Scheme 5, Step 1)

12 mmoles methyl 5,5-dimethoxypentanoate (Stevens, R. V. et al., J Am Chem Soc (1979) 7054) were dissolved in 20 ml 50% aqueous methanol. 16 mmoles NaOH were added and the mixture was stirred for 2 hr at room temperature. The solvent was then evaporated, the residue layered with 30 ml EtOAc, and the sodium salt neutralized with ice-cold 1N HCl. The aqueous phase was extracted with an additional 20 ml EtOAc, the organic extracts combined and dried over $K_2CO_3$. The product was filtered and the solvent evaporated to provide 5,5-dimethoxypentanoic acid.

Carbonyldiimidazole ($Im_2CO$, 10 mmoles) was added to a solution of 5,5-dimethoxypentanoic acid (10 mmole) in acetonitrile (13 ml), and the mixture stirred at room temperature for 40 min. Leucine benzyl ester tosylate (11 mmoles) was added, followed by diisopropylethylamine (11 mmoles), and the mixture stirred overnight at room temperature. The solvent was evaporated, and the residue dissolved in ethylacetate (50 ml), washed with ice-cold 1M citric acid (20 ml), 1M NaHCO$_3$, (20 ml) and brine (20 ml). The product was dried over MgSO$_4$, the solvent evaporated, and the residue chromatographed on silica gel to provide

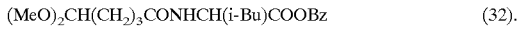

(MeO)$_2$CH(CH$_2$)$_3$CONHCH(i-Bu)COOBz    (32).

Example 31
(Scheme 5, Step 2)

Compound 32 (10 mmoles) was dissolved in 15 ml MeOH. 50 mg 10% Pd/C were added, and the mixture was hydrogenolyzed for 20 min at room temperature under 1 atm H$_2$ pressure. The mixture was then filtered and the solvent evaporated to provide (MeO)$_2$CH(CH$_2$)$_3$CONHCH(i-Bu)COOH    (33).

Example 32
(Scheme 5, Step 3)

N-aminoglycine ethylester HCl (32 mmoles) was neutralized with Na$_2$CO$_3$ (32 mmoles), extracted with CH$_2$Cl$_2$, and dried over K$_2$CO$_3$. Then, acetone (10 ml) was added, and the CH$_2$Cl$_2$ evaporated. An additional 20 ml acetone was added, and the solvent evaporated. The residue was then dissolved in CH$_2$Cl$_2$ (20 ml), dried over MgSO$_4$, and the solvent evaporated to yield Me$_2$C=NNHCH$_2$COOEt (34).

Example 33
(Scheme 5, Step 4)

Compound 34 was added to 1.1 equivalents of Boc-ala anhydride in THF and allowed to react for 12 hr. The crude product was dissolved in CH$_2$Cl$_2$, 1N HCl added, and stirred for 2 hr. The phases were then separated, and the CH$_2$Cl$_2$ evaporated to obtain Boc—NHCH(Me)CON(NH$_2$)CH$_2$COOEt    (35).

Example 34
(Scheme 5, Step 5)

Compound 35 (20 mmoles) in Et$_2$O (20 ml), was treated with NaHCO$_3$ (25 moles), Cbz—Cl (25 mmoles), and 3 drops DMF in 5 ml H$_2$O. The mixture was stirred vigorously overnight. Then 1 ml pyridine was added to destroy excess Cbz—Cl. The Et$_2$O phase was washed with 1N HCl, 1N NaHCO$_3$, and brine, dried, and the solvent evaporated. The residue was crystallized from Et$_2$O/hexane to provide Boc—NHCH(Me)CON(NH—Cbz)CH$_2$COOEt (36).

Example 35
(Scheme 5, Step 6)

The Boc protecting group was removed by reacting compound 36 with 4N HCl/dioxane for 30 min at room temperature. The excess dioxane/HCl was then evaporated to provide NH$_2$CH(Me)CON(NH—Cbz)CH$_2$COEtHCl (37).

Example 36
(Scheme 5, Step 7)

Ethyl(dimethylaminopropyl)carbodiimide (8 mmoles) was added to an ice-cooled solution of compound 31 in CH$_3$CN (15 ml), and the mixture stirred for 1 hr at 0°. Then compound 37 (8 mmoles) was added, followed by diisopropylethylamine (8 mmoles). The mixture was stirred overnight at 5° C., and the solvent evaporated. The residue was dissolved in EtOAc (30 ml), washed with ice-cold 1M citric acid (15 ml), 1M NaHCO$_3$ (15 ml) and brine (15 ml), and dried overnight over MgSO$_4$. The solvent was evaporated, and the product chromatographed on silica gel to provide

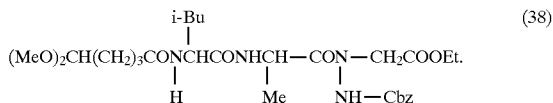

Example 37
(Scheme 5, Step 8)

Compound 38 (3 mmoles) in MeOH (15 ml) were hydrogenolyzed over 20 mg 10% Pd/C for 20 min at room temperature and under 1 atm H$_2$ pressure. The mixture was then filtered, and the solvent evaporated to provide

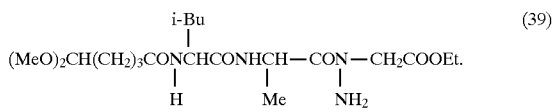

Example 38
(Scheme 5, Step 9)

Compound 39 from Example 37 was dissolved in 100 ml CH$_3$CN. Then BF$_3$·Et$_2$O (10 µl) was added, and the solution stirred overnight at room temperature. Alternatively, compound 39 (0.1 mmol) was dissolved in 1 liter of acetonitnile and p-toluene sulfonic acid (0.1 mmol) was added. After 1 hour the solvent was removed, the product dissolved in ether and washed with water and dried. The product was then treated with 2 ml trifluoroacetic acid for 20 min., concentrated and purified on a semipreparative G$_8$ reversephase HPLC column. The solvent was then evaporated, and the product chromatographed on a semi-preparative C$_4$ reverse phase HPLC column to provide the compound of the invention 40.

Example 39
(Preparation of EGF Analogs)

A synthetic polypeptide having high epidermal growth factor activity is prepared as follows:

(A) Class 1 Mimic: A compound of the formula

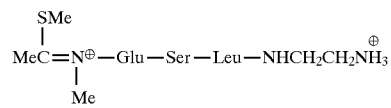

is prepared, following the procedures set forth in Examples 15–28. The compound is then cyclized following the procedure set forth in Example 29 to provide a reverse-turn stabilized EGF peptide of high activity.

(B) Class 2 Mimic: A compound of the formula

is prepared according to the procedures set forth in Examples 30–37, and is cyclized following the procedure of Example 38 to provide a small anti-parallel β-sheet reverse-turn peptide, stabilized across the β-sheet.

(C) Extended Class 2 Mimic: An extended class 2 EGF polypeptide analog is prepared similarly, by cyclizing a compound of the formula (MeO)$_2$CH(CH$_2$)$_3$CON-Met-His-Ile-Glu-Ser-Leu-Asp-Ser-Tyr-Thr-Cys-CON(NH$_2$)—CH$_2$COOEt.

Example 40
(Preparation of Malarial Antigens)

A synthetic polypeptide vaccine for malaria was recently tested in humans by Herrington et al., *Nature* (1987) 328:257. However, it proved to be only partially effective. Improvements in the potency of the vaccine could be achieved by the conformation restriction of the synthetic polypeptide, which is based upon a repeating tetrapeptide (Asn-Ala-Asn-Pro)$_3$. According to Chou-Fassam analysis (Chou et al., *Biochem* (1974) 13:222, the frame-shifted sequence Asn-Pro-Asn-Ala should have a strong tendency to form reverse turns in native proteins. The reverse turn can be locked into place by replacing putative amide-amide hydrogen bonds between Asn sidechains around proline with class 1 or class 2 hydrogen bond mimics.

(A) Class 1 Mimic: A compound of the formula

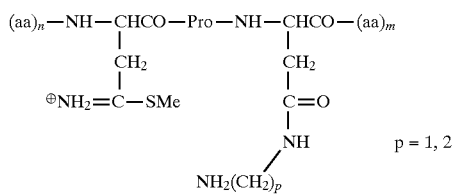

(where (aa)$_n$ and (aa)$_m$ are each independently amino acid sequences of 1–12 amino acids or R", where R" is alkyl of 1–6 carbons, phenyl, napthyl, benzyl, or —NH$_2$) is prepared following the procedures set forth in Examples 1–29, and is cyclized to form a polypeptide analog suitable for malarial vaccination having the following structure:

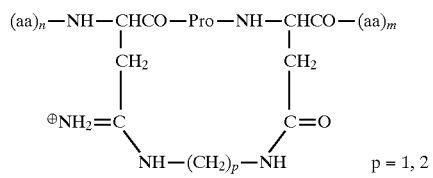

The compound is emulsified in a non-toxic vegetable oil and sterile water for injection, and is administered conventionally through intramuscular injection.

Solid Phase Synthesis

Various types of solution synthesis processes can be used in order to insert the hydrogen bond mimics of the present invention into peptides. The inclusion of Class 1 and Class 2 hydrogen bond mimics within solution synthesis procedures were disclosed above. These methods of synthesis were designed so that they could eventually be carried out on solid supports. The solid phase synthesis techniques are now disclosed below.

It is desirable to carry out solid phase synthesis procedures in connection with and including the hydrogen bond mimics because a number of advantages can be obtained. Specifically, the use of solid phase synthesis eliminates the need for purification, often eliminates intractable intermediates, and can significantly reduce the amount of time and labor required in order to obtain a given final product. Accordingly, in many situations, solid phase synthesis techniques are preferred over solution synthesis procedures.

New synthetic procedures are described herein for introducing Class 2 mimics into peptides on solid supports. Such procedures have significantly enhanced abilities with respect to utilizing Class 2 mimics in peptides. These procedures have been adapted to multiple peptide synthesis and employed to insert a variety of amino acids and variable numbers of amino acids between the hydrogen bond mimics. It is important to note that these solid phase reaction protocols can be adapted for use in connection with automated peptide synthesis machines.

Example 41

The following is a detailed description of the use of the solid phase synthesis technology of the present invention to insert Class 2 hydrogen bonds into peptides on solid supports. The results of the synthesis provide a new modified amino acid. Further, the protocol describing the insertion of a hydrazone link into the peptide is followed by a reaction scheme protocol, which should be referred to in connection with the following detailed protocol.

[(1-methylethylidene-2=FMOC) hydrazino]acetic acid. Hydrazinoacetic acid ethyl ester (15.4 gm, 100 mmol) was dissolved in 150 ml water. Then 150 ml acetone was added and the mixture heated to reflux and cooled to room temperature. The ester was then hydrolyzed by adding sodium hydroxide (8.4 g, 210 mmol) and stirring for 30 min. Then sodium carbonate (10.6 gm, 100 mmol) was added and the mixture brought to ice-cold temperature. Then FMOC-chloride (25.9 g, 100 mmol) was slowly added with stirring over a two hour period. Stirring was continued overnight while the reaction warmed to room temperature. The reaction mixture was rotary evaporated to dryness, the product dissolved in water and precipitated by acidifying with concentrated HCl. The precipitate was refluxed briefly with acetone and crystallized from ethyl acetate-hexane to give 28.4 gm (yield=81%). mp=129–131. Mass analysis, elemental analysis and NMR spectroscopy confirmed the synthesis.

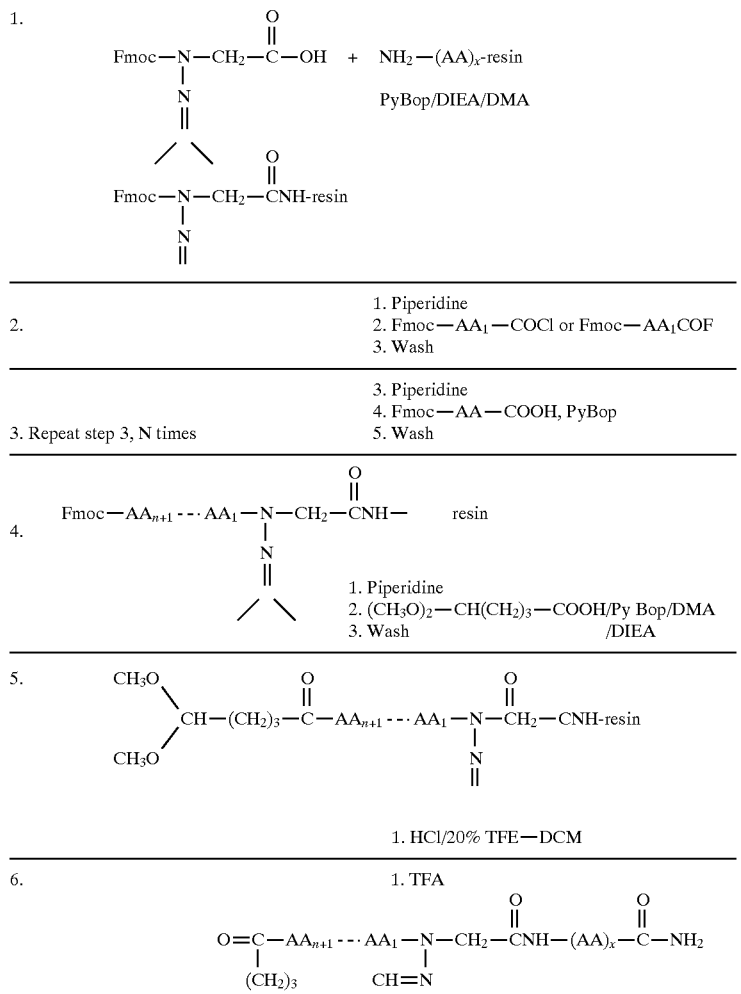

Reaction Scheme for Example 41
Insertion of Hydrogen Bond Mimic
into Peptides on Solid Support

Application of the Invention to Known Peptides

The above examples describe reaction schemes and methods of synthesizing peptides with the covalent bonds (class I or class II) in solution and on solid supports. In order to make use of these methods of synthesis the following describes how predictive algorithms can be employed to identify putative hydrogen bonds in a particular peptide of particular interest, specifically, HIV peptides. Producing such peptides with stabilized three-dimensional structures using the methods of the invention provides structures which can be used as diagnostic reagents for AIDS, panning reagents for the identification and isolation of human antibodies to HIV and synthetic vaccines produced by combining the stabilized peptides with pharmaceutically acceptable carriers.

One of the known peptides of HIV is the peptide gp120. The V3 loop of the gp120 protein has been identified as a neutralizing epitope (see W. G. Robey et al. Science 234:7023 (1987) and evidence has been cited to support the claim that gp120 is the principle neutralizing epitope (G. J. LaRosa et al., Science 249:932 (1990).

A strong correlation has been observed between the presence of antibodies to peptides from the V3 loop in seropositive mothers and the absence of disease in their children (see P. Rossi et al. P.N.A.S. 86:8055 (1989). These peptides map to the predicted hairpin and helix regions discussed below. The antibodies to either or both of the predictive loop and helix regions could be protective against HIV. More specifically, the present invention could be used to produce the loop and helix regions of the gp120 peptide and delivered to a patient in order to cause the patient to generate antibodies to these proteins and thereby provide a vaccine with respect to the AIDS virus.

The V3 loop is formed by a disulphide bridge between positions 303 and 338 of the gp120 protein. A particular type of prediction known as the GORBTURN predictions can be used in order to create predictions for the use consensus sequence for the commonly found HIVMN strain. These predictions for the consensus sequence are shown in Tables 2 and 3 below.

TABLE 2

Consensus Sequence for V3 Loop
Gorbturn Prediction of B-Turns

| LINE | RESIDUE SEQUENCE | STRENGTHS OF PREDICTION | | | B-TURN PREDICTED | |
|---|---|---|---|---|---|---|
| | | I | II | NON-SPEC | | |
| 1 | SEQ ID NO: 5 | −0.96 | −0.99 | −0.35 | | |
| 2 | SEQ ID NO: 6 | −0.80 | −0.98 | −0.93 | | |
| 3 | SEQ ID NO: 7 | −0.15 | −0.75 | 0.09 | Non-specific B-turn | |
| 4 | SEQ ID NO: 8 | −0.49 | −0.78 | 0.29 | Non-specific B-turn | |
| 5 | SEQ ID NO: 9 | 0.37 | −0.91 | 0.75 | Non-specific B-turn | |
| 6 | SEQ ID NO: 10 | −0.37 | −0.99 | −0.67 | | |
| 7 | SEQ ID NO: 11 | −0.07 | −0.97 | −0.61 | | |
| 8 | SEQ ID NO: 12 | −0.63 | −0.93 | −0.74 | | |
| 9 | SEQ ID NO: 13 | −0.71 | −0.99 | −0.37 | | |
| 10 | SEQ ID NO: 14 | −0.88 | −1.00 | −0.88 | B-strand | |
| 11 | SEQ ID NO: 15 | −0.73 | −0.99 | −0.45 | B-strand | |
| 12 | SEQ ID NO: 16 | −0.98 | −1.00 | −0.86 | B-strand | |
| 13 | SEQ ID NO: 17 | −0.57 | −1.00 | −0.87 | B-strand | |
| 14 | SEQ ID NO: 18 | −1.00 | −0.95 | 0.65 | B-strand | |
| 15 | SEQ ID NO: 19 | 0.94 | 0.99 | 0.84 | B-strand | |
| 16 | SEQ ID NO: 20 | −0.73 | 6.53 | −0.17 | Type 2 turn | |
| 17 | SEQ ID NO: 21 | −0.89 | −0.94 | −0.45 | | HAIRPIN |
| 19 | SEQ ID NO: 22 | −0.72 | −0.99 | −0.77 | | |
| 18 | SEQ ID NO: 23 | −0.59 | −1.00 | −0.89 | | |
| 20 | SEQ ID NO: 24 | −0.91 | −0.95 | −0.93 | | |
| 21 | SEQ ID NO: 25 | −0.83 | −0.98 | −0.92 | B-strand | |
| 22 | SEQ ID NO: 26 | −0.29 | −0.99 | −0.79 | B-strand | |
| 23 | SEQ ID NO: 27 | −0.71 | −0.47 | −0.54 | | |
| 24 | SEQ ID NO: 28 | −0.83 | −0.98 | −0.48 | | |
| 25 | SEQ ID NO: 29 | −0.88 | −1.00 | −0.91 | | |
| 26 | SEQ ID NO: 30 | −0.84 | −1.00 | −0.85 | | |
| 27 | SEQ ID NO: 31 | −0.91 | −0.79 | −0.38 | | |
| 28 | SEQ ID NO: 32 | −0.88 | −0.99 | 0.28 | | |
| 29 | SEQ ID NO: 33 | −0.89 | −1.00 | −0.85 | | |
| 30 | SEQ ID NO: 34 | −0.17 | −0.98 | −0.43 | N-Cap | |
| 31 | SEQ ID NO: 35 | −0.88 | −0.97 | −0.70 | Helix N1 | |
| 32 | SEQ ID NO: 36 | −0.93 | −1.00 | −0.90 | | |
| 33 | SEQ ID NO: 37 | −0.70 | −0.75 | −0.79 | Helix | |
| 34 | SEQ ID NO: 38 | −0.84 | −0.91 | −0.97 | Helix | |
| 35 | SEQ ID NO: 39 | −0.38 | −0.99 | −0.37 | Helix | |
| 36 | SEQ ID NO: 40 | −0.83 | −1.00 | −0.72 | Helix | |
| 37 | SEQ ID NO: 41 | −0.37 | −0.99 | −0.45 | | |
| 38 | SEQ ID NO: 42 | −0.78 | −0.88 | −0.38 | | |
| 39 | SEQ ID NO: 43 | −0.64 | −0.97 | −0.81 | Helix | |
| 40 | SEQ ID NO: 44 | −0.63 | −0.99 | −0.92 | Helix | |
| 41 | SEQ ID NO: 45 | −0.62 | −1.00 | −0.95 | | |
| 42 | SEQ ID NO: 46 | −0.76 | −0.94 | −0.63 | | |
| 43 | SEQ ID NO: 47 | −0.40 | −1.00 | −0.08 | | |
| 44 | SEQ ID NO: 48 | −0.01 | −1.00 | −0.74 | | |

The strength of prediction is a measure of how strongly a turn is predicted. Positive values indicate a turn type prediction; the larger the value, the stronger the turn prediction. When more than one turn type is predicted, then the turn type with the greatest strength is selected. For further details, please read the documentation.

TABLE 3

Consensus Sequence for V3 Loop
Gorbturn Prediction of B-Turns

| LINE | RESIDUE SEQUENCE | STRENGTHS OF PREDICTION | | | B-TURN PREDICTED |
|---|---|---|---|---|---|
| | | I | II | NON-SPEC | |
| 1 | SEQ ID NO: 49 | −0.93 | −1.00 | −0.92 | Helix |
| 2 | SEQ ID NO: 50 | −0.98 | −1.00 | −0.94 | Helix |
| 3 | SEQ ID NO: 51 | −0.98 | −1.00 | −0.94 | B-strand |
| 4 | SEQ ID NO: 52 | −0.90 | −0.98 | −0.68 | B-strand |
| 5 | SEQ ID NO: 53 | −0.73 | −0.96 | −0.58 | B-strand |
| 6 | SEQ ID NO: 54 | −0.49 | −0.99 | −0.47 | |
| 7 | SEQ ID NO: 55 | 0.93 | −0.94 | −0.19 | B-strand |
| 8 | SEQ ID NO: 56 | −0.78 | −0.99 | −0.63 | |
| 9 | SEQ ID NO: 57 | −0.55 | −0.99 | −0.97 | |

TABLE 3-continued

Consensus Sequence for V3 Loop
Gorbturn Prediction of B-Turns

| | | STRENGTHS OF PREDICTION | | | | |
|---|---|---|---|---|---|---|
| LINE | RESIDUE SEQUENCE | I | II | NON-SPEC | B-TURN PREDICTED | |
| 10 | SEQ ID NO: 58 | −0.12 | −0.98 | −0.79 | | |
| 11 | SEQ ID NO: 59 | −0.43 | −0.75 | −0.14 | Helix | |
| 12 | SEQ ID NO: 60 | −0.60 | −0.99 | −0.70 | | |
| 13 | SEQ ID NO: 61 | −0.07 | −0.98 | −0.79 | | |
| 14 | SEQ ID NO: 62 | −0.75 | −0.99 | −0.87 | | |
| 15 | SEQ ID NO: 63 | −0.92 | −1.00 | −0.89 | Helix | |
| 16 | SEQ ID NO: 64 | −0.92 | −1.00 | −0.91 | Helix | |
| 17 | SEQ ID NO: 65 | −0.97 | −1.00 | −0.95 | B-strand | |
| 18 | SEQ ID NO: 66 | −0.93 | −0.98 | −0.58 | B-strand | |
| 19 | SEQ ID NO: 67 | −0.93 | −0.99 | −0.91 | B-strand | |
| 20 | SEQ ID NO: 68 | −0.28 | −0.96 | −0.65 | Helix | |
| 21 | SEQ ID NO: 69 | −0.76 | −0.96 | −0.57 | | |
| 22 | SEQ ID NO: 70 | 0.03 | −0.99 | −0.53 | Type 1 turn | |
| 23 | SEQ ID NO: 71 | −0.84 | −0.99 | −0.83 | | |
| 24 | SEQ ID NO: 72 | −0.85 | −0.99 | −0.78 | | |
| 25 | SEQ ID NO: 73 | −0.95 | −1.00 | −0.91 | | |
| 26 | SEQ ID NO: 74 | −0.62 | −0.89 | −0.62 | | |
| 27 | SEQ ID NO: 75 | −0.82 | −0.92 | −0.86 | B-strand | |
| 28 | SEQ ID NO: 76 | −0.42 | −1.00 | −0.84 | B-strand | |
| 29 | SEQ ID NO: 77 | −0.96 | −0.99 | −0.35 | | |
| 30 | SEQ ID NO: 78 | −0.80 | −0.98 | −0.93 | | |
| 31 | SEQ ID NO: 79 | 0.02 | −0.63 | −0.52 | Non-specific B-turn | |
| 32 | SEQ ID NO: 80 | −0.73 | −0.96 | −0.31 | | |
| 33 | SEQ ID NO: 81 | −0.53 | −0.79 | −0.02 | | |
| 34 | SEQ ID NO: 82 | −0.82 | −0.91 | −0.55 | | |
| 35 | SEQ ID NO: 83 | 0.22 | −0.93 | −0.30 | Type 1 turn | |
| 36 | SEQ ID NO: 84 | −0.77 | −0.93 | −0.75 | | |
| 37 | SEQ ID NO: 85 | −0.73 | −0.98 | −0.38 | | |
| 38 | SEQ ID NO: 86 | −0.91 | −1.00 | −0.92 | | |
| 39 | SEQ ID NO: 87 | −0.89 | −1.00 | −0.51 | B-strand | |
| 40 | SEQ ID NO: 88 | −0.92 | −1.00 | −0.85 | B-strand | |
| 41 | SEQ ID NO: 89 | −0.98 | −0.99 | 0.35 | B-strand | |
| 42 | SEQ ID NO: 90 | −0.94 | −0.99 | −0.84 | B-strand | |
| 43 | SEQ ID NO: 91 | −0.73 | 6.53 | −0.17 | Type 2 turn | |
| 44 | SEQ ID NO: 92 | −0.89 | −0.94 | −0.45 | | HAIRPIN |
| 45 | SEQ ID NO: 93 | −0.59 | −1.00 | −0.89 | | |
| 46 | SEQ ID NO: 94 | −0.72 | −0.99 | −0.77 | | |
| 47 | SEQ ID NO: 95 | −0.91 | −0.95 | −0.93 | | |
| 48 | SEQ ID NO: 96 | −0.83 | −0.98 | −0.92 | B-strand | |
| 49 | SEQ ID NO: 97 | −0.75 | −0.99 | −0.83 | B-strand | |
| 50 | SEQ ID NO: 98 | −0.47 | −0.98 | −0.85 | B-strand | |
| 51 | SEQ ID NO: 99 | −0.34 | −0.71 | 0.19 | Non-specific B-turn | |
| 52 | SEQ ID NO: 100 | −0.77 | −1.00 | −0.80 | | |
| 53 | SEQ ID NO: 101 | −0.55 | −0.94 | 0.11 | | |
| 54 | SEQ ID NO: 102 | −0.94 | −1.00 | −0.63 | | |
| 55 | SEQ ID NO: 103 | −0.91 | −1.00 | −0.92 | B-strand | |
| 56 | SEQ ID NO: 104 | −0.52 | −0.95 | −0.63 | B-strand N-Cap. | |
| 57 | SEQ ID NO: 105 | −0.88 | −0.97 | −0.70 | B-strand N1 | |
| 58 | SEQ ID NO: 106 | −0.93 | −1.00 | −0.90 | Helix | |
| 59 | SEQ ID NO: 107 | −0.70 | −0.75 | −0.79 | B-strand | |
| 60 | SEQ ID NO: 108 | −0.84 | −0.91 | −0.97 | Helix | |
| 61 | SEQ ID NO: 109 | −0.38 | −0.99 | −0.37 | Helix | |
| 62 | SEQ ID NO: 110 | −0.83 | −1.00 | −0.72 | Helix | HELIX |
| 63 | SEQ ID NO: 111 | −0.37 | −0.99 | −0.45 | | |
| 64 | SEQ ID NO: 112 | −0.78 | −0.88 | −0.38 | | |
| 65 | SEQ ID NO: 113 | −0.64 | −0.97 | −0.81 | | |
| 66 | SEQ ID NO: 114 | −0.63 | −0.99 | −0.92 | Helix | |
| 67 | SEQ ID NO: 115 | −0.62 | −1.00 | −0.95 | | |
| 68 | SEQ ID NO: 116 | −0.78 | −0.90 | −0.78 | | |
| 69 | SEQ ID NO: 117 | −0.24 | −1.00 | −0.41 | | |
| 70 | SEQ ID NO: 118 | 0.43 | −1.00 | −0.72 | | |
| 71 | SEQ ID NO: 119 | −0.59 | −0.99 | −0.78 | Helix | |
| 72 | SEQ ID NO: 120 | −0.56 | −0.79 | −0.77 | Helix | |
| 73 | SEQ ID NO: 121 | −0.77 | −0.98 | −0.76 | Helix | |
| 74 | SEQ ID NO: 122 | −0.96 | −1.00 | −0.89 | Helix | |
| 75 | SEQ ID NO: 123 | −0.94 | −1.00 | −0.93 | Helix | |
| 76 | SEQ ID NO: 124 | −0.93 | −0.96 | −0.69 | Helix | |
| 77 | SEQ ID NO: 125 | −0.75 | −0.97 | −0.83 | Helix | |
| 78 | SEQ ID NO: 126 | −0.56 | −0.98 | −0.75 | Helix | |
| 79 | SEQ ID NO: 127 | −0.80 | −0.99 | −0.92 | Helix | |
| 80 | SEQ ID NO: 128 | −0.46 | −0.90 | −0.62 | Helix | |

TABLE 3-continued

Consensus Sequence for V3 Loop
Gorbturn Prediction of B-Turns

| LINE | RESIDUE SEQUENCE | STRENGTHS OF PREDICTION | | | B-TURN PREDICTED |
|---|---|---|---|---|---|
| | | I | II | NON-SPEC | |
| 81 | SEQ ID NO: 129 | −0.35 | −1.00 | −0.74 | Helix |
| 82 | SEQ ID NO: 130 | −0.88 | −0.98 | −0.79 | Helix |
| 83 | SEQ ID NO: 131 | −0.86 | −0.95 | −0.96 | Helix |
| 84 | SEQ ID NO: 132 | −0.42 | −0.26 | −0.51 | Helix |
| 85 | SEQ ID NO: 133 | −0.72 | −0.98 | −0.69 | Helix |

The strength of prediction is a measure of how strongly a turn is predicted. Positive values indicate a turn type prediction; the larger the value, the stronger the turn prediction. When more than one turn type is predicted, then the turn type with the greatest strength is selected. For further details, please read the documentation.

The consensus sequence predictions suggest a structural motif which has also been predicted by a neural network analysis of the V3 region from 245 different HIV-1 isolates (see G. J. LaRosa et al. cited above). These algorithms predict a secondary structure motif for the V3 loop consisting of a B strand—Type II reverse turn—B strand—alpha helix. It should be noted that a B strand—type II reverse turn—B strand is a characteristic of a B-hairpin loop.

An analysis of mutational frequencies provide additional information with regards to structure. B-hairpins are often characterized by a hydrogen bonding pattern where alternate pairs of amino acids have hydrogen bonds across the strand. Mutational frequencies for amino acids in the predictive strand regions (see G. J. LaRosa et al. cited above) display a remarkable cadence consistent with a 2:2 B-hairpin structure. However, predictive algorithms and mutational analysis do not rule out the presence of other structures such as the 2:4, 3:3, 3:5, 4:4, 4:6 or other irregular B-hairpin loops for the consensus sequence RKSIHIGPGRAFYTTG and all B-hairpin structures should be considered possible until experimentation and results eliminates a possibility. Hairpin loops are classified here according to the nomenclature of B. L. Sibanda et al., J. Mol. Biol. 206:759 (1989). The predicted structures provide information with regard to where hydrogen bond mimics might be initially inserted.

The prediction for an alpha helix at the C-terminus of the V3 loop is also strengthened by the analysis of mutations in the putative N-cap and N1 positions. It has been observed that the most frequently found amino acids at the N-cap position are Ser, Asn, Gly, Asp and Thr (J. S. Richardson and D. C. Richardson, Science 240:1648 (1988). These preferences are a consequence of the ability of the amino acid side chain to hydrogen bond to the backbone amide NH of the N2 or more preferably the N3 amino acids. This side chain to backbone hydrogen bonding stabilizes the otherwise non-hydrogen bonded backbone amide protons at the N-termini of alpha helices. It was also observed that Pro and Glu are most often found at the N1 position. The observed N-cap and N1 amino acids are often treated as helix breakers i.e. Asp and Pro and thus are not predicted to be helix by algorithms (see Tables 2, 3 above).

The HIV loop mutates frequently at the putative N-cap and N1 positions and less in the extension of the predicted helical region. Frequently, these mutations are to those favored at helix start positions adding considerable strength to the prediction for alpha helix initiation at these positions. Thus one observes Asn-Met (BH10), Thr-Ileu (NM), Asp-Ileu (SC) and Lys-Pro (HIVII) at the N-cap and N1 positions while remaining amino acids in the predicted HIV1 helices, RQAHCNISRAK SEQ ID NO:139 remain invariant. In addition to strengthening the prediction for a helix, this analysis points out another feature which may be of use from the viewpoint of hydrogen bond mimics, namely that a side-chain to backbone hydrogen bond is predicted from the N-cap to the N2 or N3 position.

To summarize, predictive algorithms and mutational analyses lead to a self consistent and detailed structural model of the loop region with a hydrogen bonding pattern that provides a rational starting point for the insertion of hydrogen bond mimics. A predicted hydrogen bonding map for a consensus sequence (G. J. LaRosa et al., referenced above) for the loop region is shown in FIG. 1.

The predicted structure displays a 2:2 B hairpin structure. However, it is not intended to rule out other potential loops and B-hairpin structures and is merely meant to be illustrative. In addition, the longest potential alpha helix is indicated. It could be shorter with a C-terminus at Asn, Arg or Lys or at other positions.

Both the Class I and Class II hydrogen bond mimics have been employed to conformationally restrict V3 loop peptides as well as other peptides to smaller loop and alpha helical structures. Some of these peptides which include V3 loop peptides were synthesized using methods of synthesis in solution described above while others including the V3 helix peptides were synthesized by adding a preformed [Leu-Ala] NucSite to a peptide on a solid support (also described above). Either method can be used to synthesize helicized peptides.

Figure 2:
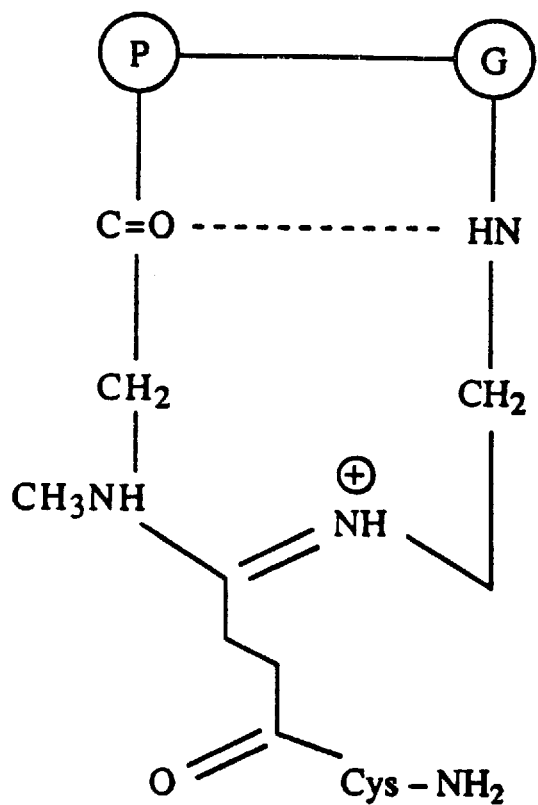
FIG. 2 is a schematic view of HIV compound 1.
Figure 3:
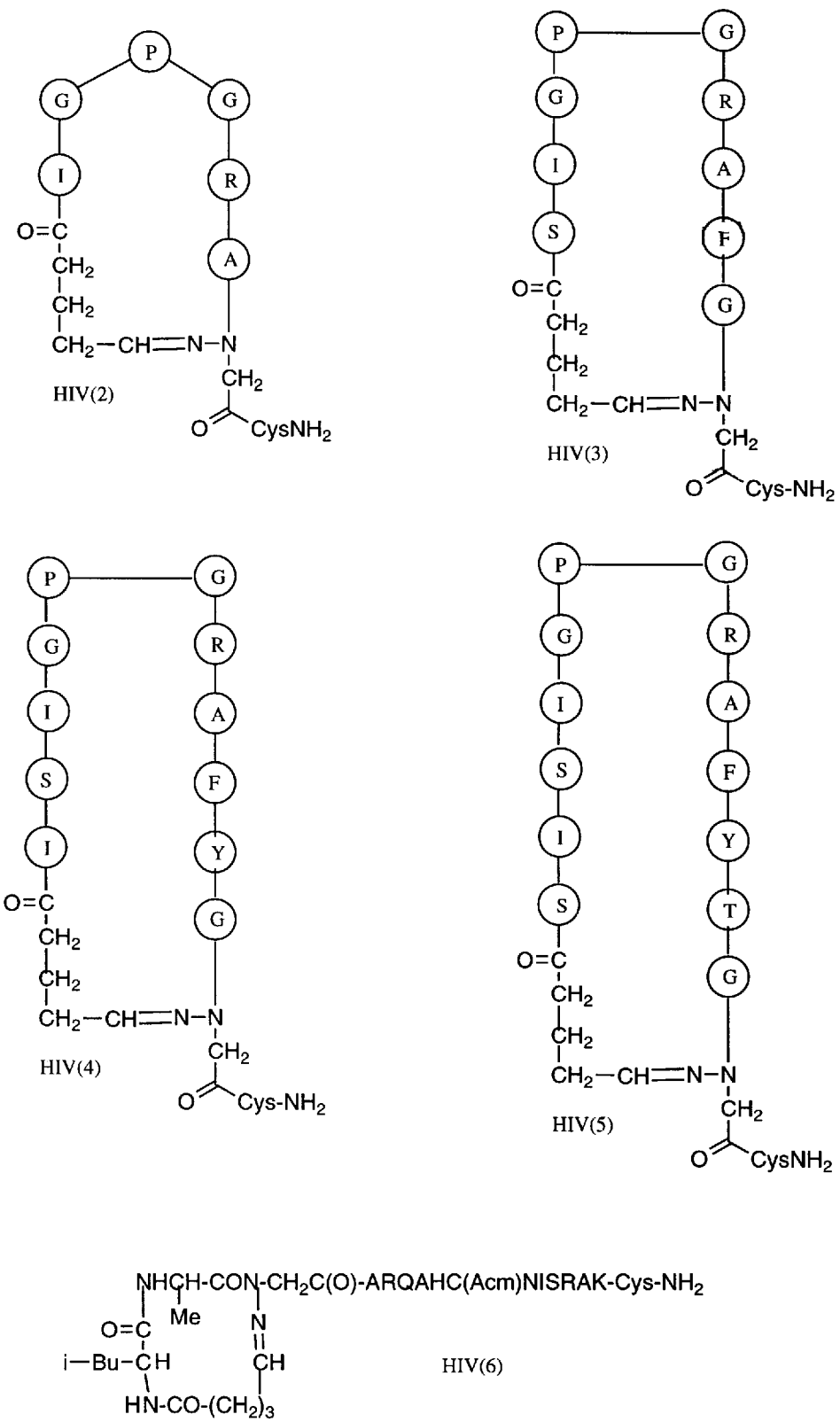
FIG. 3 is a schematic view showing HIV compounds 2–6.

Each of the hydrogen bonds in the proposed B hairpin can be replaced with either the Class I or the Class II mimic according to FIGS. 2 and 3. The Class I mimic replaces hydrogen bonds in the (i, i+n) sense while the Class II mimic acts in the alternative (i+n, i) sense.

Each structure can be tagged at the base of the loop with cysteine or other linkers for attachment to supports of interest i.e. maleimide activated BSA or KLH for immunizations. Modified versions of the Class I linker has been prepared for this purpose.

Example 42

The compound Cbz—NHCH$_2$CONHCH$_2$COBz is synthesized by coupling Cbz—NHCH$_2$CH$_2$COOH to the glycine benzyl ester (NH$_2$CH$_2$COOBz) using standard procedures with an equivalent of DCC in DMF.

Example 43

The compound FmocNHCH(CH$_2$NHBOC)COOH is synthesized by first making Cbz—NHCH(CH$_2$NH—Boc)CO$_2$H according to the procedure of M. Waki et al.

Synthesis, pp. 266–267 (1981). The Cbz group is removed with 10% Pd-C/hydrogen gas in ethanol and then treated with commercially available Fmoc-Cl using standard procedures to give FmocNHCH(CH$_2$NHBOC)COOH.

Example 44

The compound FmocNHYCH$_2$CH(NHBoc)COOH is synthesized by first making Boc—NHCH(CH$_2$NH$_2$)COOH according to the method of M. Waki et al. (cited above). This product is treated with Fmoc-Cl to give FmocNHYCH$_2$CH(NHBoc)COOH using procedures shown in Scheme 6 below.

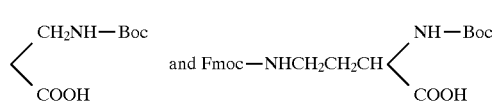

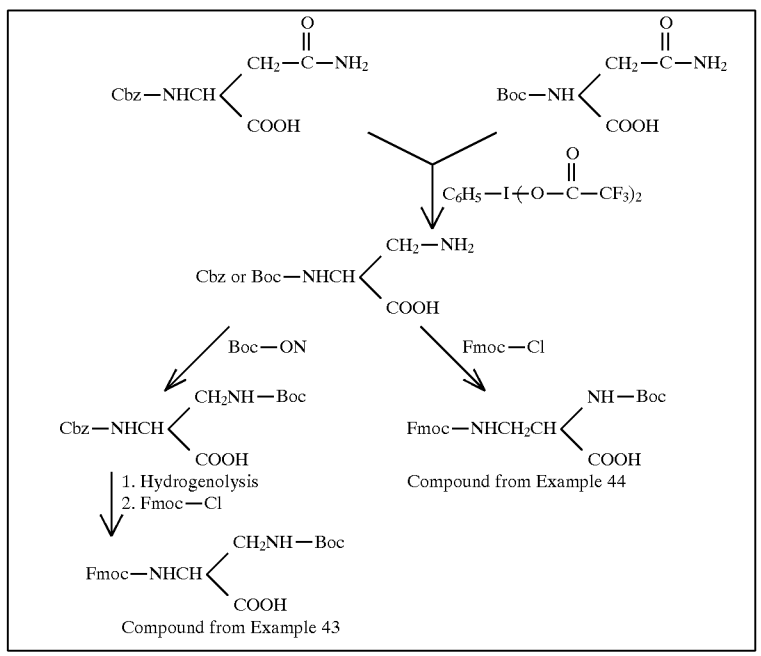

The compounds of Examples 43 and 44 were used to incorporate the Class I mimic into peptides on solid supports utilizing the procedures outlined in Scheme 7 below.

Scheme 7
Synthesis of cyclic peptide turns on solid supports

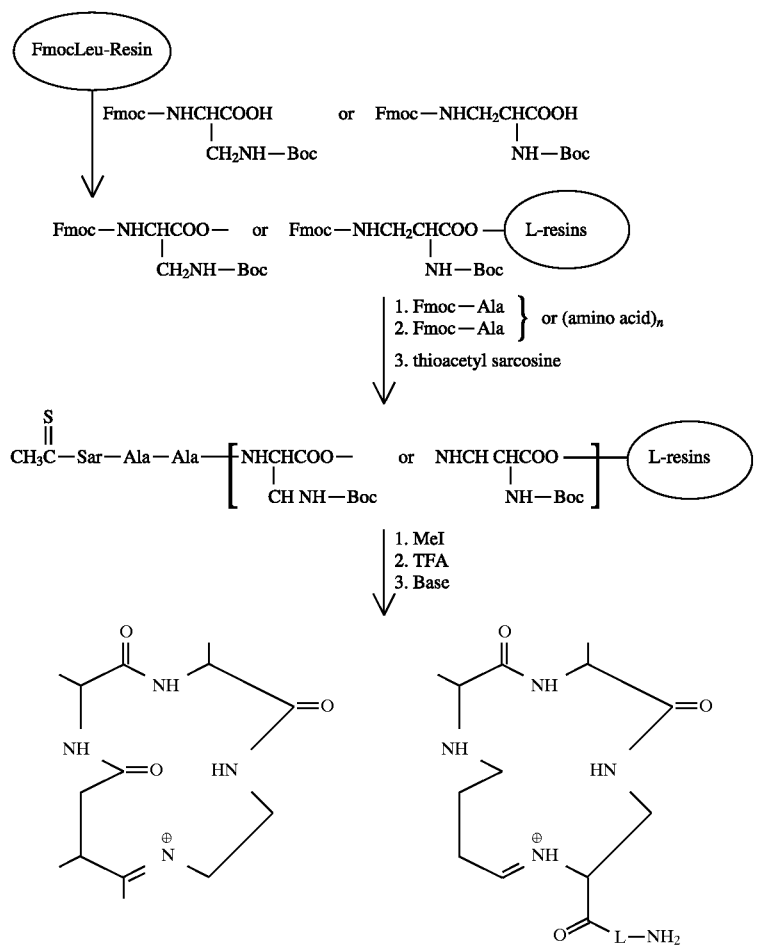

These procedures utilize standard fMOC chemistry for the initial coupling of FmocLeu to RINK'S RESIN TM, a polystyrene resin with a cleavable linker of 4-(2', 4'-dimethoxyphenyl-Fmoc-aminomethyl)phenol, hereinafter referred to as "Rink's amide resin", followed by the sequential coupling of either Compounds of Examples 43 or 44, FmocALA and FmocALA. The peptide is then capped with acetyl thiosarcosine. Coupling is carried out using a standard PyBOP/HOBt/DIEA coupling scheme. Final cyclization is achieved by treating the capped peptide on the solid support with methyl iodide in acetic acid for 20 hours. The resin is then washed and the activated precyclic intermediate cleaved from the resin with 10% trifluoroacetic acid/methylene chloride and concentrated by rotary evaporation. The final Boc protecting group on the cleaved peptide is removed with trifluroacetic acid in 5 min and the peptide concentrated by rotary evaporation. The activated precyclic is dissolved in DMF and treated with BIORAD™ AG4-X4 anion exchange resin which frees the amine for cyclization. After filtration to remove resin, the product is concentrated and purified by HPLC.

The mass spectrum of the isolated products from syntheses with either compounds of Examples 43 or 44 were identical to that for the expected cyclized product. 1D NMR spectra for both compounds were consistent with the incorporation of a Class 1 mimic. The 1D NMR spectrum for the compound incorporating compound 3 was of the pattern expected for a Type 1 reverse turn. However, the NMR spectrum for the cyclic peptide formed with compound of Example 44 was not characteristic of a Type 1 reverse turn. It is likely that both links can be used in larger loops.

Example 45

The compound FmocNHCH$_2$CSNHCH$_2$CH$_2$COOH is synthesized according to Scheme 8. First BocNHCH$_2$CH$_2$NH$_2$ is synthesized according to P. L. Barker et al. J. Org. Chem 46: 2455–2465 (A980).

Scheme 8

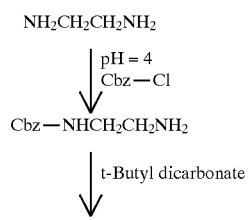

51

-continued
Scheme 8

Cbz—NHCH₂CH₂NH—Boc

↓ H₂, Pd

NH₂CH₂CH₂NH—Boc

↓ Cl—C(=O)—CH₂CH₂—COOC₂H₅

Boc—NHCH₂CH₂NH—C(=O)—CH₂CH₂—COOC₂H₅

↓ LW reagent
  NaOH

Boc—NHCH₂CH₂NH—C(=S)—CH₂CH₂COOH

↓ HCl, Dioxane
  Fmoc—Cl

Fmoc—NHCH₂CH₂NH—C(=S)—CH₂CH₂—COOH

The initial compound is mixed with commercially available $ClCOCH_2CH_2COOC_2H_5$ in DMF to give $BocNHCH_2CH_2NHCOCH_2COOC_2H_5$. This product is treated with Lawesson's reagent to give the thioamide. Then the ethyl ester is hydrolyzed with sodium hydroxide in ethanol. The Boc group is then removed with 4N HCl in dioxane and the final product formed by treating with commercially available FmocCl using standard procedures. The product has been identified by mass spectroscopy and NMR.

Example 46

Compound 6 of Example 6 is used for the introduction of the Class I link into peptides on solid support (Scheme 9).

Cyclization Scheme 9

Fmoc—NHCH₂CH₂NH—C(=S)—CH₂CH₂CONH—(Resin)

↓ Solid phase peptide synthesis

NH₂—(Amino Acid)ₙ—NHCH₂CH₂NH—C(=S)—CH₂CH₂—CONH—(resin)

↓ 1. MeI/Acetic acid
  2. DIEA
  3. TFA

52

-continued
Cyclization Scheme 9

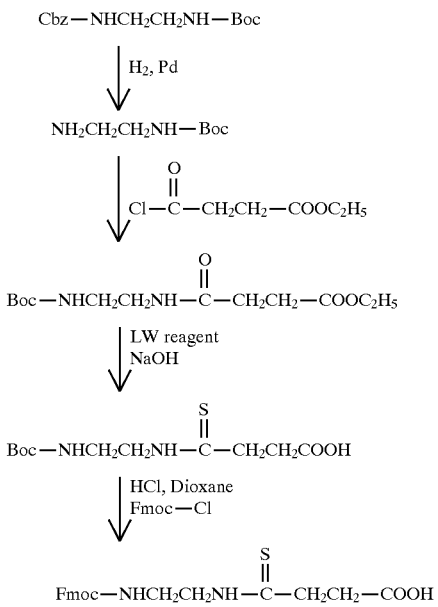

The initial target is referred to here as HIV compound 1 shown in FIG. 2.

Compound 6 linked to Rink's amide resin using DIC and HOBT. The compound is then extended with amino acids utilizing standard Fmoc chemistry already described (PyBOP/HOBT/DIEA). The final amino acid will be freed of its Fmoc group. The thioamide will then be activated with methyl iodide/acetic acid. The addition of DIEA should then lead to cyclization on the solid support. One advantage of the method is that standard Boc/But side chain protection can be used for protecting amino acids in these reactions. These protecting groups are stable to acetic acid. Also, any basic amino groups, i.e. N-terminal amino acid will be protonated and protected from methylation. The cyclic peptide product would then be cleaved from the resin and side chains deprotected with 5% water/95% trifluroacetic acid and the final product purified by HPLC.

Class II Mimics

The following include Class II mimic to provide conformationally restricted HIV peptides shown below and referred to as HIV compounds 2, 3, 4, 5 and 6.

HIV(2): cyclic peptide G-I-P-G-G
with side chain O=C-CH₂-CH₂-CH₂-CH=N-N-CH₂-C(=O)-CysNH₂
(R, A included in ring)

HIV(3): cyclic peptide P-G-G-R-A-F-G
with side chain O=C-CH₂-CH₂-CH₂-CH=N-N-CH₂-C(=O)-Cys-NH₂
(I, S included in ring)

-continued

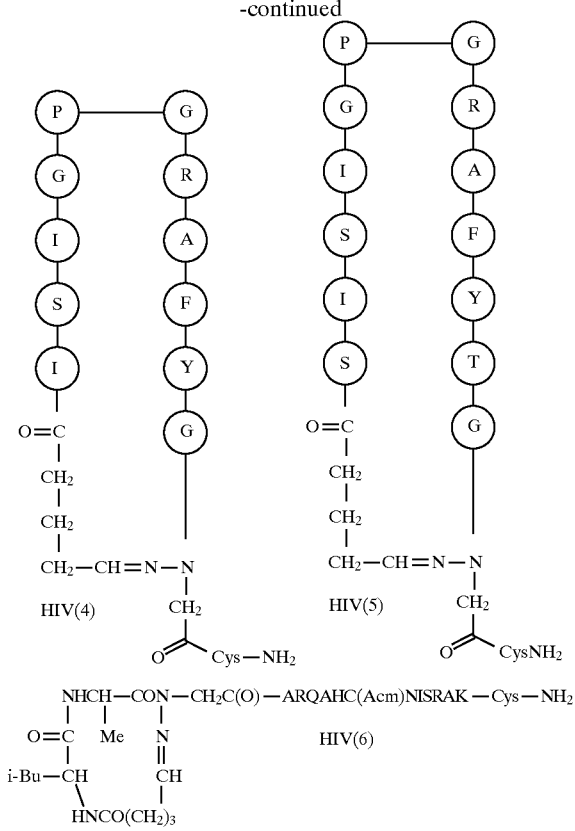

These sequences use SISI at the N-terminus rather than the consensus sequence, SIHI, or the HIVMN sequence RIHI. The HIV peptides shown above were synthesized on solid supports utilizing the method described above. The only difference in the procedures is that FmocGly chloride is used in place of FmocAla chloride and that the longer amino acid sequences corresponding to the HIV sequences were incorporated between J and Z. J is 5,5-dimethoxypentanoic acid which is described in Example 30. Numerous variations on this theme can be imagined using different mutant sequences, linked together at different positions.

All products gave the correct mass by mass spectroscopy. A signal corresponding to that expected for the N=CH proton was apparent in 1D NMR spectra HIV(1) (4) and (5) above. Signals from Phe and/or Tyr overlap this signal in 1D NMR spectra for HIV (2) above; insufficient quantities were available for examining the NMR spectrum for HIV (3) above. A preliminary examination of temperature coefficients for the amide NH protons of HIV (4) above reveal them to be >6 ppb per K; this indicates that the loop as constituted is highly flexible. The introduction of further constraints i.e. diethylglycine-Z in place of GZ might be used to decrease the flexibility.

Example 47

[LeuAla]NucSite was synthesized by treating compound 40 (70 mg) with NaOH (15 mg) in 50% ethanol-water (20 ml) with stirring for 2.5 hr. The reaction mixture was then acidified with prewashed Dowex 50W-X4 cation exchange resin for 15 min, filtered, concentrated and lyophilized to yield 65 mg of product. The primary structure was confirmed by high resolution mass spectroscopy and NMR.

Example 48

Compound HIV (6) above was synthesized by first using standard Fmoc chemistry (PyBOP/HOBt/DIEA) to give SEQ ID NO:135-Rink amide resin. Then [LeuAla]NucSite was linked to the peptide chain on the resin using the standard coupling reaction. The peptide was cleaved from the resin as previously described and protecting groups removed with three rounds of treatment with 5% water/95% trifluoroacetic acid for 1 hr and precipitation of the peptide with ether. The peptide is then purified to homogeneity by HPLC and its primary structure confirmed by mass spectroscopy and 1D NMR. The 1D NMR spectrum is characteristic of a peptide that has been helicized.

Biological Tests on the HIV Peptides

The compounds HIV (3) and HIV (5) were found to bind to three murine monoclonals which also bind HIV. At least one of these monoclonals have been found to protect in monkey challenge experiments with HIV. The compounds HIV (3), (5) and (6) have been shown to react positively using ELISA with sera from a patient with AIDS. HIV (5) has been used to isolate human Fabs from combinatorial libraries by panning. Previous attempts to isolate human Fabs to this critical epitope using peptides had not worked. These Fabs could provide a component for engineered human Mabs that could play a role in the passive immunotherapy of AIDS patients. Each and all of the compounds HIV (1)–(6) are potential synthetic vaccines for protection against HIV. Each has been linked via Cys to maleimide activated protein carriers for immunization purposes.

Example 49

$FmocNHCH(CH_2CH_2CH(OCH_3)_2)COOH$ could be made by the synthesis outlined in Scheme 10 with references to similar syntheses.

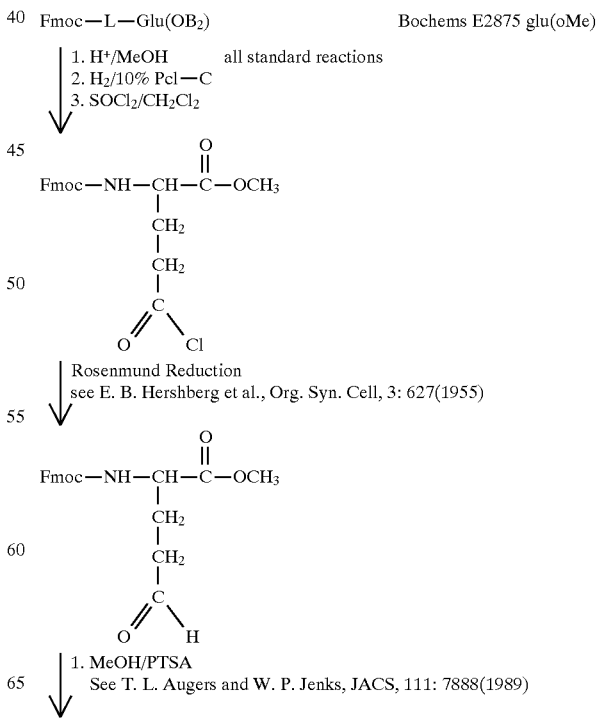

-continued
Scheme 10

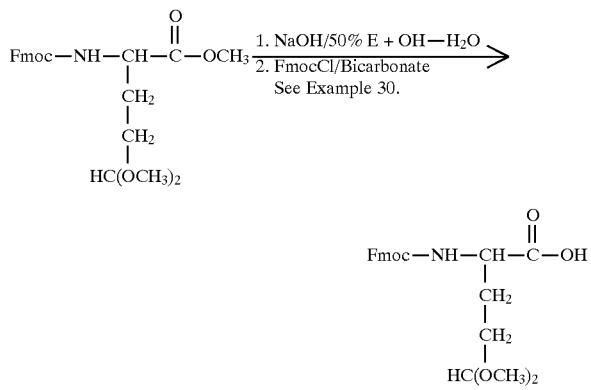

Such a reaction scheme can be employed for substituting a Class II mimic for the hydrogen bond which is often observed between the carboxyl group oxygen of the N-cap Asp or Asn side chains and the mainchain amide NHY proton of the N-cap+3 amino acid. An argument (above) has been made for the existence of this structure in the HIV V3 loop. This link allows one to insert a hydrogen bond mimic into the middle of an amino acid sequence thus allowing one to covalently link different conformationally restricted structural units.

The procedure of Example 49 could be utilized for linking the "B-hairpin" region and the alpha helical region of the V3 loop into one structure. An ability to link two secondary structures could favor the formation of a supersecondary structure particularly in the context of a disulfide loop. This larger structure could reconstitute conformational epitopes and prove useful as an improved panning reagent or vaccine.

Since the introduction of hydrogen bond mimics on solid supports can be automated and in fact is in the process of being automated at this time, these larger structures are potentially accessible.

HELICIZED PEPTIDES

Example 50

[LeuAla]NucSiteALFQKEKMVLGGCG-NH2 SEQ ID NO:145 was synthesized in the same manner as Example 49. It has been extensively characterized in 1D and 2D NMR experiments and found to form significant fraction of full length alpha helix in water.

Example 49 contains an epitope from Patarroyo's malaria vaccine (M. E. Patarroyo et al., (1988) Nature 332:158). This epitope is predicted to be alpha helical by GORB-TURN.

[LeuAla]NucSite was found to increase the efficacy of this epitope in a monkey challenge trial with P. falciparum merozoites, the major form of human malaria. Challenge experiments were carried out.

Example 51

SEQ ID NO:136 was synthesized on solid support using methods described above. This demonstrates that longer peptides can be helicized by inserting the Class II mimic into peptides on a solid support. It was identified by mass spectroscopy and the 1D NMR spectra of this peptide in water is consistent with the presence of substantial fraction of alpha helix.

The compound of Example 51 was synthesized as a potential mimic for the glucocorticoid receptor DNA-binding domain. NMR spectroscopy reveals the cognate sequence is helical in the protein (T. Hard et al., Science 249:157 (199)) and X-ray crystallogrpahy shows it binding specifically to the major groove (B. F. Luisi et al., Science 352:497 (1991). The helix could be responsible for DNA recognition. Reagents that show specificity for DNA sequences are potential anticancer drugs.

The instant invention is shown and described herein in what is considered to be the most practical, and preferred embodiments. It is recognized, however, that departures may be made therefrom which are within the scope of the invention and that obvious modifications will occur to one skilled in the art upon reading this disclosure.

What is claimed:

1. A compound which mimics the V3 loop of gp 120 of HIV having binding activity with respect to anti-HIV antibodies, the compound being represented by the following structure (SEQ ID NO: 141):

wherein I represents isoleucine, G represents glycine, P represents proline, R represents arginine and A represents alanine.

2. A compound which mimics the V3 loop of gp 120 of HIV having binding activity with respect to anti-HIV antibodies, the compound being represented by the following structure (SEQ ID NO: 142):

wherein S represents serine, I represents isoleucine, G represents glycine, P represents proline, R represents arginine, A represents alanine, and F represents phenylalanine.

3. A compound which mimics the V3 loop of gp 120 of HIV having binding activity with respect to anti-HIV antibodies, the compound being represented by the following structure (SEQ ID NO: 143):

```
    P ——— G
    |     |
    G     R
    |     |
    I     A
    |     |
    S     F
    |     |
    I     Y
    |     |
   O=C    G
    |     |
   CH₂    |
    |     |
   CH₂    |
    |     |
   CH₂—CH=N—N
                |
HIV(4)         CH₂
                |
               O=C—Cys—NH₂
``` wherein S represents serine, I represents isoleucine, G represents glycine, P represents proline, R represents arginine, A represents alanine, F represents phenylalanine and Y represents tyrosine.

4. A compound which mimics the V3 loop of gp 120 of HIV having binding activity with respect to anti-HIV antibodies, the compound being represented by the following structure (SEQ ID NO: 144):

```
    P ——— G
    |     |
    G     R
    |     |
    I     A
    |     |
    S     F
    |     |
    I     Y
    |     |
    S     T
    |     |
   O=C    G
    |     |
   CH₂    |
    |     |
   CH₂    |
    |     |
   CH₂—CH=N—N
                |
HIV(5)         CH₂
                |
               O=C—CysNH₂
``` wherein S represents serine, I represents isoleucine, G represents glycine, P represents proline, R represents arginine, A represents alanine, F represents phenylalanine, Y represents tyrosine and T represents threonine.

5. A compound which mimics the V3 loop of gp 120 of HIV having binding activity with respect to anti-HIV antibodies, the compound being represented by the following structure (SEO ID: 134):

```
      NHCH—CON—CH₂C(O)—ARQAHC(Acm)NISRAK—Cys—NH₂
       |   |     |
      O=C  Me    N              HIV(6)
       |         ||
   i-Bu—CH       CH
         \      /
         HNCO(CH₂)₃
``` wherein A represents alanine, R represents arginine, Q represents glutamine, H represents histidine, C represents cysteine, (Acm) represents acetylated methionine, N represents asparagine, I represents isoleucine, S represents serine and K represents lysine.

* * * * *